(12) United States Patent
Yoshida et al.

(10) Patent No.: US 12,239,379 B2
(45) Date of Patent: Mar. 4, 2025

(54) OPHTHALMIC APPARATUS, METHOD FOR CONTROLLING OPHTHALMIC APPARATUS, AND STORAGE MEDIUM

(71) Applicant: CANON KABUSHIKI KAISHA, Tokyo (JP)

(72) Inventors: Hirofumi Yoshida, Kanagawa (JP); Yuki Shimozato, Tokyo (JP); Hayato Shioda, Kanagawa (JP); Shinya Tanaka, Tokyo (JP); Kazuhide Miyata, Kanagawa (JP); Ritsuya Tomita, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 651 days.

(21) Appl. No.: 17/502,854

(22) Filed: Oct. 15, 2021

(65) Prior Publication Data

US 2022/0117486 A1    Apr. 21, 2022

(30) Foreign Application Priority Data

Oct. 20, 2020 (JP) .................... 2020-176077
Dec. 9, 2020 (JP) .................... 2020-204332
Aug. 23, 2021 (JP) .................... 2021-135543

(51) Int. Cl.
A61B 3/15   (2006.01)
A61B 3/00   (2006.01)
A61B 3/10   (2006.01)
A61B 3/12   (2006.01)

(52) U.S. Cl.
CPC ............ *A61B 3/152* (2013.01); *A61B 3/0041* (2013.01); *A61B 3/102* (2013.01); *A61B 3/12* (2013.01)

(58) Field of Classification Search
CPC ....... A61B 3/152; A61B 3/0041; A61B 3/102; A61B 3/12; A61B 3/0016; A61B 3/0025; A61B 3/0075; A61B 3/1225; A61B 3/14; A61B 3/15
See application file for complete search history.

(56) References Cited

FOREIGN PATENT DOCUMENTS

JP         2014039870 A     3/2014
WO     WO-2014091992 A1 *  6/2014    ........... A61B 3/0025

* cited by examiner

*Primary Examiner* — Tuyen Tra
(74) *Attorney, Agent, or Firm* — Canon U.S.A., Inc. IP Division

(57) ABSTRACT

An ophthalmic apparatus includes an inspection unit configured to inspect an eye to be inspected, a driving unit configured to drive the inspection unit, and a control unit configured to start control of the inspection unit and the driving unit based on an inspection protocol in response to a predetermined condition, the inspection protocol defining a series of control procedures for performing a plurality of inspections including an alignment adjustment for aligning the inspection unit with the eye to be inspected, wherein the control unit is configured to display results of the plurality of inspections and display information for accepting an instruction to retry a part of the plurality of inspections on a display unit.

24 Claims, 19 Drawing Sheets

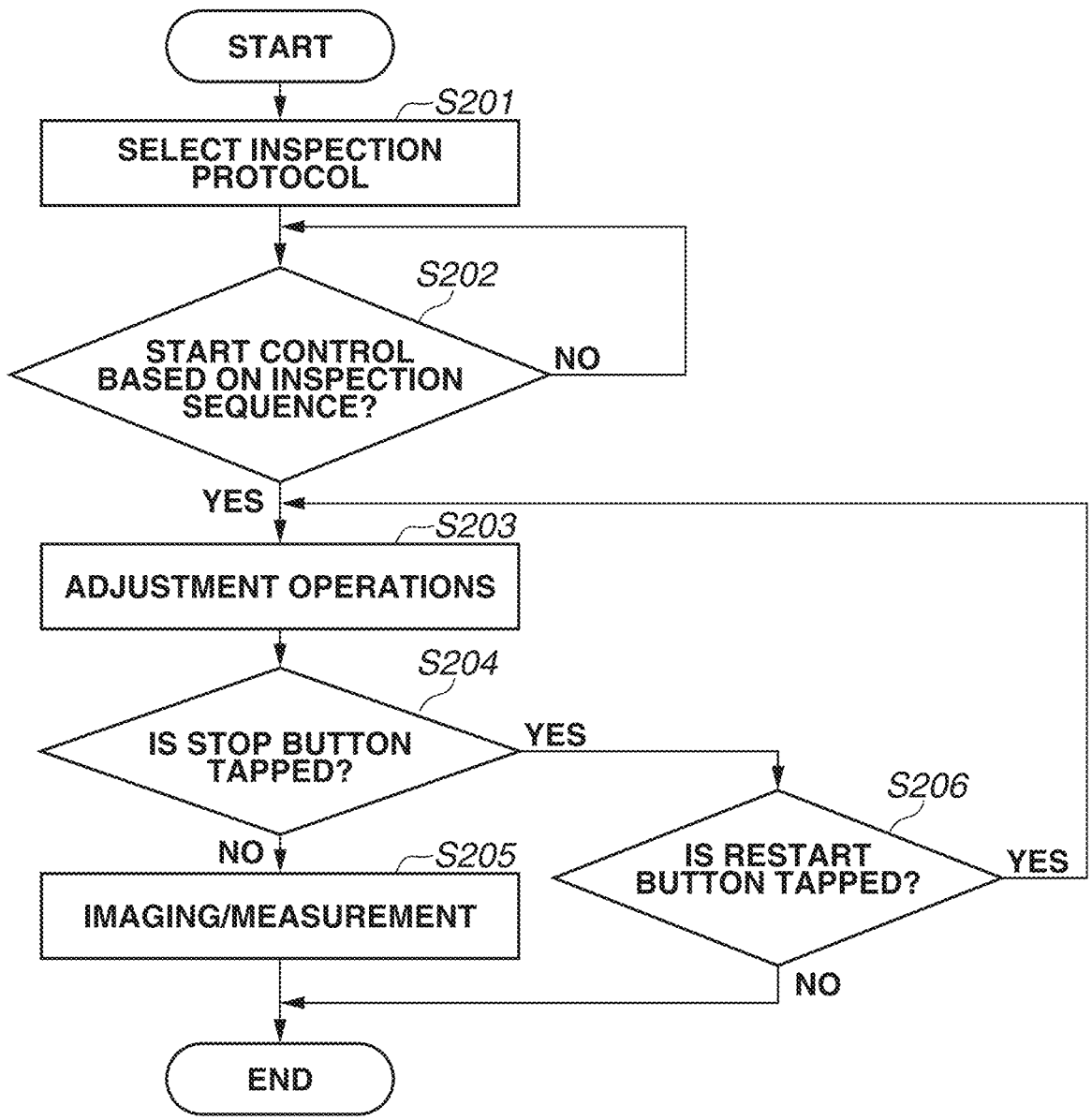

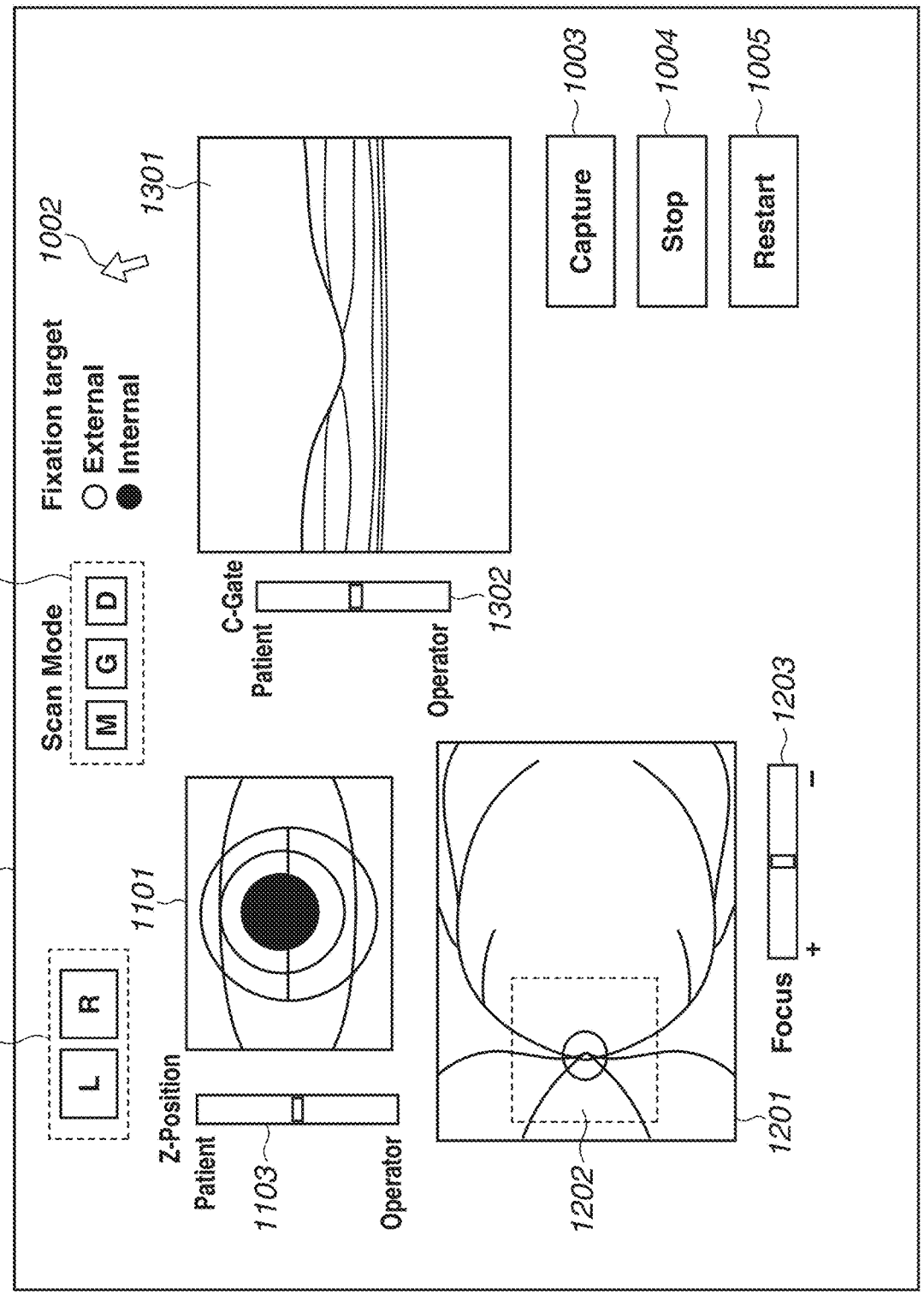

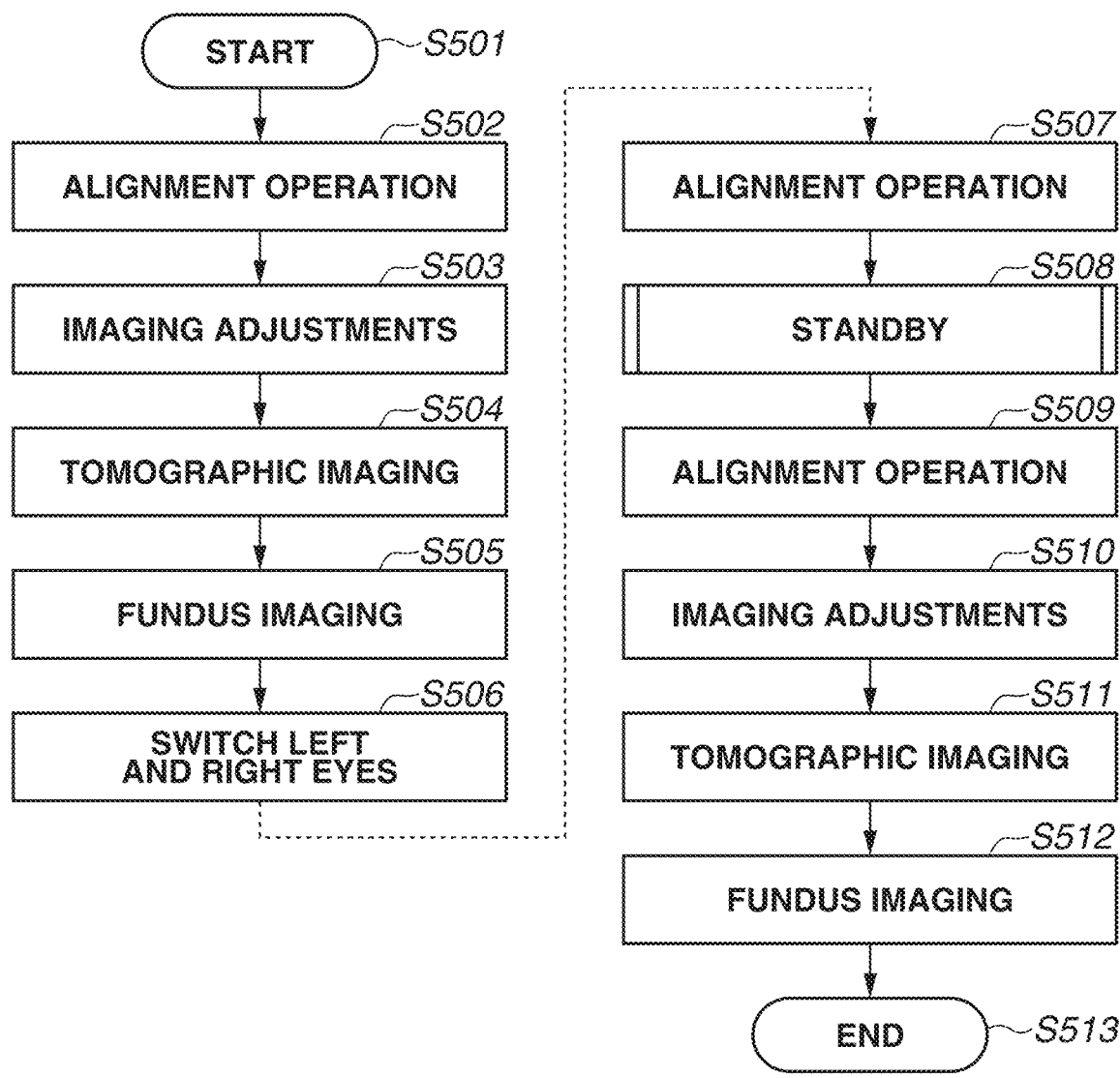

OPHTHALMIC APPARATUS, METHOD FOR CONTROLLING OPHTHALMIC APPARATUS, AND STORAGE MEDIUM

BACKGROUND

Field of the Disclosure

The present disclosure relates to an ophthalmic apparatus, a method for controlling an ophthalmic apparatus, and storage medium.

Description of the Related Art

Apparatuses for obtaining a two-dimensional fundus image of an eye to be inspected (hereinafter, referred to as fundus camera apparatuses) and apparatuses for obtaining a tomographic image of an eye to be inspected by using optical coherence tomography (OCT) with low-coherence light (hereinafter, referred to as OCT apparatuses) have been put to practical use as ophthalmic apparatuses.

In such apparatuses, an alignment adjustment between the apparatus and an eye to be inspected and other adjustments are performed before capturing an image. Ophthalmic apparatuses having an automatic function of automatically making such adjustments have been developed in recent years. By using the automatic function, the user can easily use the ophthalmic apparatuses to capture an image of an eye to be inspected without complicated adjustment operations.

Japanese Patent Application Laid-Open No. 2014-39870 discusses an optical image measurement apparatus having a function of obtaining a fundus tomographic image and a fundus image. The optical image measurement apparatus discussed in Japanese Patent Application Laid-Open No. 2014-39870 also has a function of automating imaging operations, such as automatic imaging and automatic focusing. In the optical image measurement apparatus discussed in Japanese Patent Application Laid-Open No. 2014-39870, a scan mode is selected in advance from among a plurality of scan modes for signal light with which the fundus is scanned. In a case where the function of automating the imaging operations is on, a fundus tomographic image and a fundus image are automatically obtained based on the selected scan mode.

SUMMARY

According to an aspect of the present invention, an ophthalmic apparatus includes an inspection unit configured to inspect an eye to be inspected, a driving unit configured to drive the inspection unit, and a control unit configured to start control of the inspection unit and the driving unit based on an inspection protocol in response to a predetermined condition, the inspection protocol defining a series of control procedures for performing a plurality of inspections including an alignment adjustment for aligning the inspection unit with the eye to be inspected, wherein the control unit is configured to display results of the plurality of inspections and display information for accepting an instruction to retry a part of the plurality of inspections on a display unit.

Further features of the present invention will become apparent from the following description of exemplary embodiments with reference to the attached drawings.

BRIEF DESCRIPTION OF THE DRAWINGS

FIG. 9 is a flowchart illustrating an example of a measurement procedure according to a second exemplary embodiment.

FIG. 10 is a diagram illustrating an example of an imaging screen according to the second exemplary embodiment.

FIG. 13 is a flowchart illustrating an example of an inspection protocol according to the third exemplary embodiment.

DESCRIPTION OF THE EMBODIMENTS

Figure 1:
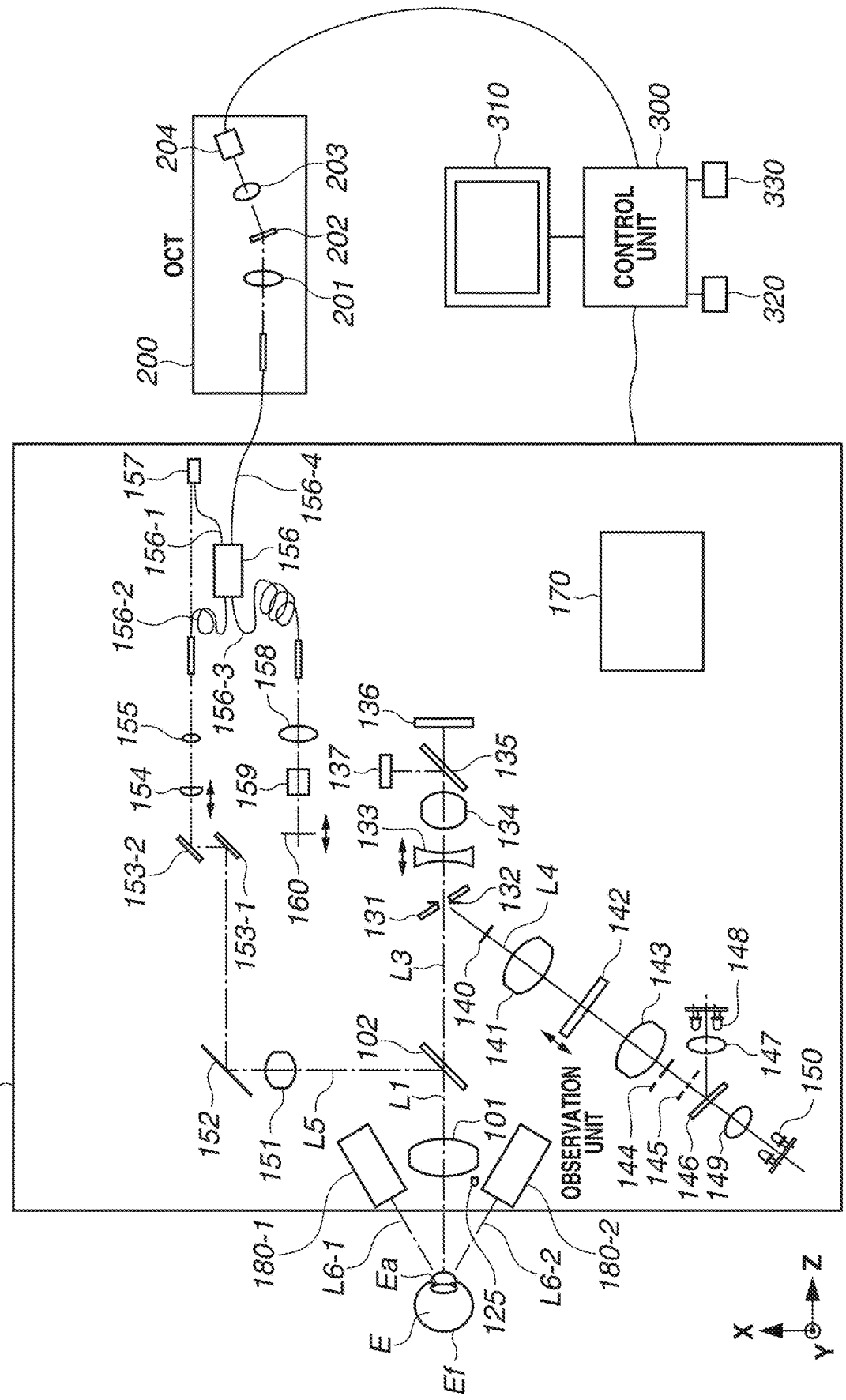
FIG. 1 is a diagram illustrating a schematic configuration example of an ophthalmic apparatus according to a first exemplary embodiment.

Exemplary embodiments of the present invention will be described in detail below with reference to the drawings. Note that dimensions, materials, shapes, and relative positions of components described in the following exemplary embodiments are optional and can be modified depending on the configuration of the apparatuses to which the exemplary embodiments are applied and various conditions. In the drawings, reference numerals are consistently used to represent the same or functionally similar elements.

In a first exemplary embodiment, an ophthalmic apparatus for performing both optical coherence tomography (OCT) imaging and visible light fundus imaging will be described as an example of the ophthalmic apparatus according to an exemplary embodiment of the present invention. Conventional optical image measurement apparatuses end operations after storing obtained interference images and color fundus images. For example, in a case where imaging is to be retried under the same conditions as a series of imaging operations that has been performed or in a case where a part of a series of imaging operations that has been performed is to be retired, a user returns to an imaging conditions specifying step to specify the same conditions again and then performs the same operations again from the beginning, and this becomes a cause of low usability. The present exemplary embodiment is directed to improving the usability of the ophthalmic apparatus. The ophthalmic apparatus according to the present exemplary embodiment stores a plurality of inspection protocols each defining a series of control procedures including both OCT imaging and visible light fundus imaging, and the user can select one of the inspection protocols and execute control based on the selected inspection protocol.

The ophthalmic apparatus according to the present exemplary embodiment displays a fundus image obtained by fundus imaging, an OCT image obtained by OCT imaging, and an imaging button on a display unit. The imaging button is an example of display information for accepting an instruction to perform at least either one of the fundus imaging and the OCT imaging. In a case where the imaging button is operated, the ophthalmic apparatus according to the present exemplary embodiment performs the instructed inspection(s) under the same conditions as with the inspections defined in the selected inspection protocol without displaying a screen that is displayed to prompt the user to select an inspection protocol.

An ophthalmic system according to the present exemplary embodiment may be configured in such a way that the ophthalmic apparatus (composite inspection unit) according to the present exemplary embodiment is connected to a network, receives an order (written inspection directions) from a doctor's personal computer, performs inspections on an eye to be inspected based on the order, and transmits a result of the inspection to the doctor's personal computer.

<Apparatus Configuration>

The ophthalmic apparatus used in the present exemplary embodiment includes a fundus imaging unit that captures a two-dimensional fundus image and an OCT imaging unit that obtains a tomographic image of the eye to be inspected using combined light (interference light) obtained by combining return light from the eye to be inspected irradiated with measurement light with reference light. A configuration using a fundus camera that illuminates the fundus with visible light and captures a color image will be described as an example of the fundus imaging unit, whereas color scanning laser ophthalmoscopy (SLO) imaging of scanning the fundus with visible light and obtaining a color fundus image may be used.

In the following description, an adjustment operation for imaging and an imaging operation which are performed in succession will be collectively referred to as an inspection. Information defining execution of a plurality of such inspections in succession will be referred to as an inspection protocol. The operation to be performed in an inspection may be measurement of eye characteristics instead of imaging Examples of the measurement include eye pressure, axial length, refractive power, cornea curvature, pupil diameter, and wavefront aberration measurements, and a retina thickness measurement in an OCT inspection.

The term protocol is typically used in the meaning of a procedure, system, or rules. In the field of communications, a protocol refers to rules defining an information format and communication procedures in particular. As employed herein, an inspection protocol refers to information defining procedures for performing a plurality of inspections. An inspection protocol may define both inspection conditions and inspection procedures. Examples of the imaging conditions in performing imaging as an inspection include a scan pattern, a scan range, and a portion to be scanned.

The first exemplary embodiment will be described below with reference to FIG. 1, which illustrates a schematic configuration and optical systems of the ophthalmic apparatus according to the present exemplary embodiment.

In the following description, a direction substantially the same as the line of sight direction of an eye E to be inspected will be referred to as a Z direction. A plane perpendicular to the Z direction will be referred to as an XY plane. An X direction refers to a horizontal direction, and a Y direction a vertical direction.

The ophthalmic apparatus includes an optical head unit 100 that is an example of an inspection unit, a spectrometer 200, and a control unit 300 that is an example of a control unit. While the ophthalmic apparatus is described to include such units inside, the control unit 300 and the spectrometer 200 may be disposed outside the ophthalmic apparatus main body. A part of the optical head unit 100 may be disposed outside the ophthalmic apparatus. The configuration of the optical head unit 100, the spectrometer 200, and the control unit 300 will be described below in order.

<Configuration of Optical Head Unit 100 and Spectrometer 200>

The optical head unit 100, an example of the inspection unit, includes an optical system for capturing an image of an anterior eye part Ea of the eye E to be inspected and a measurement optical system for capturing a two-dimensional fundus image and a three-dimensional tomographic image (OCT image) of a fundus Ef of the eye E to be inspected. Various optical systems included in the optical head unit 100 will be described below.

The optical head unit 100 includes an objective lens 101 provided at a position opposed to the eye E to be inspected. A first dichroic mirror 102 functioning as an optical path separation unit is disposed on an optical axis L1 of the objective lens 101. The first dichroic mirror 102 branches the optical path on the optical axis L1 into an optical path for a fundus imaging system (optical axis L3) and an optical path for an OCT interference system (optical axis L5) based on the wavelength bands.

A perforated mirror 131, an imaging diaphragm 132, a focus lens 133, an imaging lens 134, a third dichroic mirror 135, and an image sensor 136 are arranged on the optical axis L3 in a transmission direction of the first dichroic mirror 102. The perforated mirror 131 has an opening in its center. The focus lens 133 moves on the optical axis L3 to adjust focus. The third dichroic mirror 135 branches the optical path on the optical axis L3 into an optical path leading to the image sensor 136 and an optical path leading to a fixation lamp 137, based on the wavelength bands. The image sensor 136 is a fundus image sensor that is sensitive to both visible light and infrared rays and is used for both moving image observation and still image capturing. The fixation lamp 137 produces visible light to prompt an examinee to visual fixation.

A cornea baffle 140, a relay lens 141, a focus index unit 142, a lens 143, and a ring slit 144 are arranged in this order on an optical axis L4 in a reflection direction of the perforated mirror 131. The cornea baffle 140 has a light shielding point at the center. The ring slit 144 has an annular slit opening. A lens baffle 145 and a second dichroic mirror 146 are arranged on the optical axis L4. The lens baffle 145 serves as a light shielding member having a light shielding point. The second dichroic mirror 146 has a characteristic of transmitting infrared rays and reflecting visible light. The focus index unit 142 can be moved along the optical axis L4 and can be inserted and removed into/from the optical path on the optical axis L4.

A condenser lens 147 and a white light-emitting diode (LED) light source 148 are arranged in a reflection direction of the second dichroic mirror 146. The white LED light source 148 is an imaging light source including a plurality of white LEDs emitting pulsed visible light. A condenser lens 149 and an infrared LED light source 150 are arranged in a transmission direction of the second dichroic mirror 146. The infrared LED light source 150 is an observation light source including a plurality of infrared LEDs emitting constant infrared rays. The objective lens 101, the second dichroic mirror 146, the optical members disposed in between the objective lens 101 and the second dichroic mirror 146, and the condenser lenses 147 and 149 are included in an illumination optical system for illuminating the fundus. The fundus Ef of the eye E to be inspected is illuminated with the light from the white LED light source 148 or the infrared LED light source 150 via the illumination optical system.

A lens 151, a mirror 152, an OCT X scanner 153-1, an OCT Y scanner 153-2, and lenses 154 and 155 are arranged on the optical axis L5 in a reflection direction of the first dichroic mirror 102. Each of the OCT X scanner 153-1 and the OCT Y scanner 153-2 includes a mirror, for example, and functions as a scanning unit for scanning the fundus Ef of the eye E to be inspected with measurement light. The OCT X scanner 153-1 and the OCT Y scanner 153-2 are disposed in such a way that the vicinities of their center positions come to the focal position of the lens 151. The vicinities of the center positions are optically conjugate with the position of the pupil of the eye E to be inspected. Such a configuration makes the optical path with the scanning unit as an object point substantially parallel between the objective lens 101 and the lens 151. The incident angle of the measurement light incident on the first dichroic mirror 102 located between the objective lens 101 and the lens 151 can thus be maintained the same while the OCT X scanner 153-1 and the OCT Y scanner 153-2 scan the fundus Ef with the measurement light. The OCT X scanner 153-1 and the OCT Y scanner 153-2 scan the measurement light in a main scanning direction and a sub scanning direction orthogonal to the main scanning direction, respectively. However, the scanning directions are not limited thereto.

A measurement light source 157 is a light source emitting light for obtaining the measurement light to be input into a measurement optical path. In the present exemplary embodiment, the measurement light in the OCT optical system is emitted with a fiber end as a light source. The fiber end is optically conjugate with the fundus Ef of the eye E to be inspected. The lens 154 is a lens for focus adjustment, and driven in an optical axis direction illustrated by the arrow in the diagram by a not-illustrated motor. The focus adjustment for the measurement light is performed in such a way that the measurement light emitted from the fiber end serving as the light source forms an image on the fundus Ef. The lens 154 functioning as a focus adjustment unit is disposed between the fiber end serving as the measurement light source and the OCT X and Y scanners 153-1 and 153-2 functioning as the scanning unit. By such a focus adjustment, the image of the measurement light emitted from the fiber end can be formed on the fundus Ef of the eye E to be inspected, and return light from the fundus Ef can be efficiently returned to an optical fiber 156-2.

In FIG. 1, the optical path between the OCT X scanner 153-1 and the OCT Y scanner 153-2 is disposed within the plane of the diagram. In fact, the optical path is directed orthogonal to the plane of the diagram.

Next, a configuration of the optical path from the measurement light source 157, a reference optical path, and the spectrometer 200 will be described. The measurement light source 157, an optical coupler 156, optical fibers 156-1 to 156-4, a lens 158, a dispersion compensation glass 159, a reference mirror 160, and the spectrometer 200 are included in a Michelson interference system. The optical fibers 156-1 to 156-4 are single-mode optical fibers integrally connected by the optical coupler 156. The light emitted from the measurement light source 157 is guided to the optical coupler 156 via the optical fiber 156-1. The light guided to the optical coupler 156 is split into measurement light in the optical fiber 156-2 and reference light in the optical fiber 156-3. The measurement light is passed through the optical path of the foregoing OCT optical system to irradiate the fundus Ef of the eye E to be inspected that is the observation target. The measurement light is reflected and scattered by the retina and reaches the optical coupler 156 again through the same optical path.

Meanwhile, the reference light reaches the reference mirror 160 via the optical fiber 156-3, the lens 158, and the dispersion compensation glass 159, and is reflected. The dispersion compensation glass 159 is inserted to match the dispersion of the reference light with that of the measurement light. The reference light reflected by the reference mirror 160 returns through the same optical path and reaches the optical coupler 156 again. The reference light and the measurement light (return light) reached the optical coupler 156 again are combined by the optical coupler 156. The measurement light and the reference light here cause interference due to the combination if an optical path length of the measurement light and an optical path length of the reference light are substantially the same. The reference mirror 160 is supported in such a way that a position of the reference mirror 160 can be adjusted in the optical axis direction illustrated by the arrow in the diagram by a not-illustrated motor and driving mechanism. By using the motor and the adjustment mechanism, the optical path length of the reference light can be adjusted to the optical path length of the measurement light, which varies depending on the eye E to be inspected. The combined light is guided to the spectrometer 200 via the optical fiber 156-4.

The spectrometer 200 includes a lens 201, a diffraction grating 202, a lens 203, and a line sensor 204. The combined light emitted from the optical fiber 156-4 is turned into substantially parallel light through the lens 201, and then spectrally dispersed by the diffraction grating 202 and focused on the line sensor 204 by the lens 203. Each element of the line sensor 204 outputs a signal corresponding to the received light. The control unit 300 samples the signals at a predetermined timing by using an image obtaining unit 304 to be described below, and applies predetermined signal processing to the signals to generate a tomographic image.

Next, the surroundings of the measurement light source 157 will be described. In the present exemplary embodiment, the measurement light source 157 uses a super luminescent diode (SLD) that is a typical low coherent light source. The light emitted from the measurement light source 157 has a central wavelength of 855 nm and a wavelength bandwidth of approximately 100 nm. Bandwidth is an important parameter since bandwidths affect resolution of the obtained tomographic image in the optical axis direction. While the SLD is selected here as the type of light source, the measurement light source 157 may be of any type as long as low coherent light can be emitted. An amplified spontaneous emission (ASE) source can be also used. In view of eye measurement, the central wavelength of the measurement light is desirably near infrared. The central wavelength is desirably as short as possible since the central wavelength affects lateral resolution of the obtained tomographic image. For both the reasons, light having a central wavelength of 855 nm is used in the present exemplary embodiment.

While in the present exemplary embodiment a Michelson interferometer is used as the interferometer, a Mach-Zehnder interferometer may be used. The Mach-Zehnder interferometer is desirably used if a light amount difference between the measurement light and the reference light is large. The Michelson interferometer is desirably used if the light amount difference is relatively small.

Stereoscopic cameras 180-1 and 180-2 each including a lens and an image sensor are disposed on optical axes L6-1 and L6-2 different from the optical axis L1, respectively. The stereoscopic cameras 180-1 and 180-2 are examples of an observation unit. For anterior eye observation, the stereoscopic cameras 180-1 and 180-2 are disposed on the XZ plane on the optical axis L1, substantially symmetrically with respect to the optical axis L1, and substantially simultaneously capture stereoscopic images of the anterior eye part Ea of the eye E to be inspected in different directions. Pixel values obtained by the stereoscopic cameras 180-1 and 180-2 are output to a display unit 310 that is an example of the display unit via the control unit 300. The display unit 310 may be a touch panel to which the user can input instructions by tapping. Here, the user's touching operation on the touch panel will be referred to as a tap. An anterior eye part observation light source 125 disposed near the objective lens 101 illuminates the anterior eye part Ea of the eye E to be inspected.

The stereoscopic cameras 180-1 and 180-2 here are disposed on the XZ plane on the optical axis L1, substantially symmetrically with respect to the optical axis L1. However, the stereoscopic cameras 180-1 and 180-2 may be disposed at positions shifted in the Y direction to reduce an effect of vignetting from eyelashes and an eyelid. The optical head unit 100 may include three or more stereoscopic cameras 180 instead of two.

The optical head unit 100 includes a head driving unit 170 that is an example of a driving unit for driving the inspection unit. The head driving unit 170 includes three not-illustrated motors, and is configured in such a way that the optical head unit 100 can be moved in three-dimensional (X, Y, and Z) directions with respect to the eye E to be inspected. This enables alignment adjustments to the optical head unit 100 with respect to the eye E to be inspected.

<Configuration of Control Unit 300>

Figure 2:
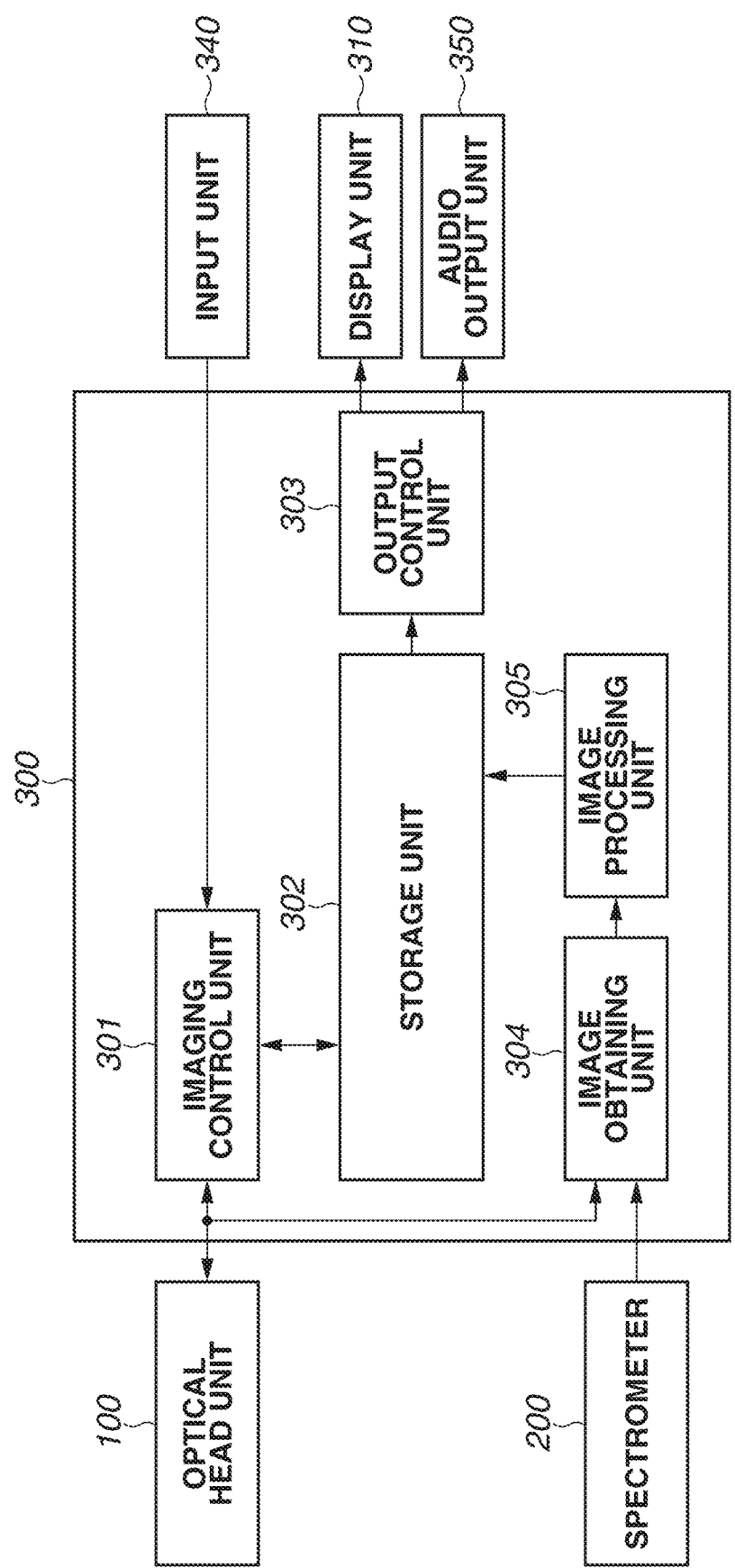
FIG. 2 is a diagram illustrating a schematic configuration example of a control unit of the ophthalmic apparatus according to the first exemplary embodiment.

Next, a schematic configuration of the control unit 300 will be described with reference to FIG. 2. The control unit 300 includes an imaging control unit 301, a storage unit 302 that is an example of a storage unit, an output control unit 303 that is an example of a notification unit, the image obtaining unit 304, and an image processing unit 305.

The imaging control unit 301 is connected to the storage unit 302, the optical head unit 100, and an input unit 340. A touch panel to which the user can input instructions by tapping may be provided to serve as both the display unit 310 and the input unit 340. The imaging control unit 301 receives an input signal from the input unit 340, and controls the components of the optical head unit 100 based on an inspection protocol stored in the storage unit 302. The input unit 340 includes a not-illustrated mouse and keyboard.

The storage unit 302 stores inspection protocols, generated images of the eye E to be inspected, image analysis results, imaging conditions in obtaining the images, and information about the eye E to be inspected. The storage unit 302 also stores various programs for controlling the ophthalmic apparatus.

According to the present exemplary embodiment, an inspection protocol is information defining a series of control procedures for performing a plurality of inspections. Here, an inspection includes adjustment operations including an alignment adjustment and operations for capturing an image. A plurality of inspection protocols is stored in the storage unit 302 in advance. The user selects one of the plurality of inspection protocols on a not-illustrated inspection protocol selection screen, and issues an instruction to execute control based on the selected inspection protocol. The processing procedures defined by an inspection protocol may include information about the imaging conditions, such as a scan pattern and a portion to be scanned. The scan pattern and the portion to be scanned will be described below. An inspection protocol may include control procedures based on an order received via a not-illustrated network. In such a case, the ophthalmic apparatus may receive order information including patient information, an inspection mode, and a portion to be inspected via the network, store the order information in the storage unit 302, and subsequently transmit information about inspection results stored in the storage unit 302 to a personal computer issued the instruction.

The image obtaining unit 304 is connected to the storage unit 302, the optical head unit 100, the spectrometer 200, and the image processing unit 305. The image obtaining unit 304 is further connected to the stereoscopic cameras 180-1 and 180-2 in the optical head unit 100, and generates anterior eye part images of the eye E to be inspected and transmits the anterior eye part images to the image processing unit 305. The image obtaining unit 304 is also connected to the image sensor 136 in the optical head unit 100, and generates a fundus image of the eye E to be inspected and transmits the fundus image to the image processing unit 305. The image obtaining unit 304 is also connected to the line sensor 204 in the spectrometer 200, and generates a tomographic image of the eye E to be inspected and transmits the tomographic image to the image processing unit 305.

The image processing unit 305 processes the anterior eye part images, the fundus image, and the tomographic image obtained by the image obtaining unit 304, and transmits the processed images to the storage unit 302. The image processing unit 305 analyzes the anterior eye part images, detects relative position information about the eye E to be inspected and the optical head unit 100, and transmits the relative position information to the storage unit 302.

The output control unit 303 is connected to the display unit 310, such as a display, that is an example of the display unit. The output control unit 303 can display the anterior eye part images, the fundus image, and the tomographic image of the eye E to be inspected, and the analysis result obtained by the image processing unit 305 on the display unit 310. The display unit 310, an example of the display unit, may be a touch panel to which the user can makes an input by touching. The user's touching operation on the touch panel is referred to as a tap. The output control unit 303 is connected to an audio output unit 350 that is an example of a notification unit, and can make an audio output of the analysis result obtained by the image processing unit 305 and a warning to the user.

The control unit 300 may include a selection unit for selecting one of the plurality of inspection protocols based on the user's instructions.

The control unit 300 described above may include modules to be executed by a central processing unit (CPU) or a micro processing unit (MPU), or a circuit that implements specific functions like an application specific integrated circuit (ASIC). The storage unit 302 may be implemented by using a storage medium such as a memory and an optical disc.

<Method for Displaying Anterior Eye Part Moving Image>

Next, a method for displaying the anterior eye part images of the eye E to be inspected obtained by the stereoscopic cameras 180-1 and 180-2 according to the present exemplary embodiment will be described.

Since the stereoscopic cameras 180-1 and 180-2 are disposed on the optical axes L6-1 and L6-2 different from the optical axis L1, the anterior eye part images obtained by image obtaining unit 304 are horizontally distorted images viewed in the directions of the optical axes L6-1 and L6-2 (horizontally sideways).

The image processing unit 305 performs projective transformation to transform the distorted anterior eye part images into images viewed in the direction of the optical axis L1 (from the front) (image transformation means). The transformed coordinates (x', y') of each pixel in the images can be determined from the coordinates (x, y) before the transformation and transformation coefficients (a, b, c, d, e, f, g, and h) by the following Eqs. (1) and (2):

$$x' = \frac{xa + yb + c}{xg + yg + 1}, \text{ and} \quad (1)$$

$$y' = \frac{xd + ye + f}{xg + yg + 1}. \quad (2)$$

The transformation coefficients (a, b, c, d, e, f, g, and h) can be determined if there are four or more sets of corresponding points obtained before and after the transformation. The transformation coefficients can be determined by calibration during assembly or upon startup of the ophthalmic apparatus.

Figure 11A:
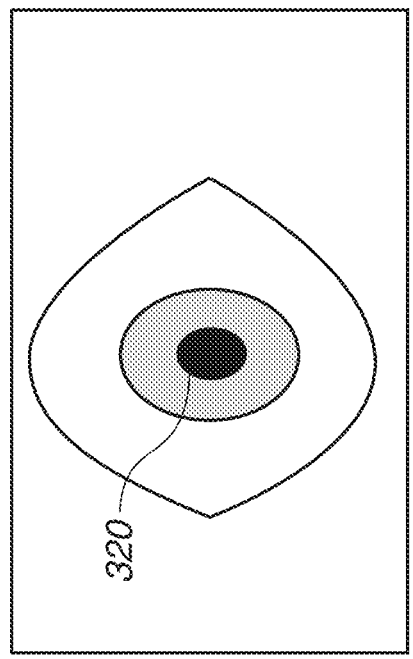
FIG. 11A is a diagram illustrating an example of an anterior eye part image obtained in exemplary embodiments.
Figure 11B:
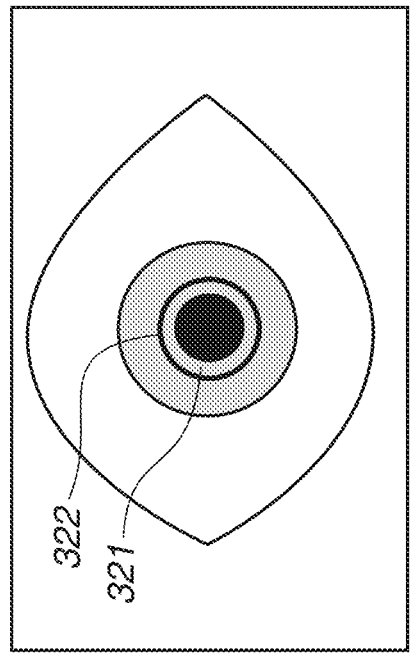
FIG. 11B is a diagram illustrating an example of an image obtained by transforming the anterior eye part image according to exemplary embodiments.

FIG. 11A illustrates an anterior eye part image obtained by either one of the stereoscopic cameras 180-1 and 180-2. FIG. 11B illustrates the transformed anterior eye part image.

The image processing unit 305 transforms the captured anterior eye part images at regular intervals, and transmits the transformed images to the storage unit 302. The output control unit 303 reads the transformed images from the storage unit 302 at regular intervals, and displays a transformed anterior eye part moving image on the display unit 310.

The images to be displayed as a moving image here may be at least either one or both of the anterior eye part images obtained by the stereoscopic cameras 180-1 and 180-2.

A pupil 320 in FIG. 11A looks like a horizontally-constricted substantial ellipse, which makes it difficult for the user to find out a pupil state, such as a pupil diameter. A pupil 321 in FIG. 11B looks like a substantially perfect circle, and the user can easily find out the pupil state, such as a pupil diameter.

In displaying the transformed anterior eye part moving image on the display unit 310, the output control unit 303 superimposes a circular alignment reference mark 322 as illustrated in FIG. 11B (alignment reference mark generation means). The position of the alignment reference mark indicates an alignment target position. The size of the circle indicates the size of a minimum pupil diameter for the inspection.

Such a display of the anterior eye part moving image improves user's operability in standby and resuming operations based on the pupil state during the inspection, and thus stable inspection results can be obtained with high efficiency.

<Method for Detecting Relative Position Information>

Next, a method for detecting the relative position information about the optical head unit 100 with respect to the eye E to be inspected by using the stereoscopic cameras 180-1 and 180-2 according to the present exemplary embodiment will be described.

The image processing unit 305 calculates the relative position information (positional deviation amounts) about the eye E to be inspected and the optical head unit 100 in the X, Y, and Z directions by analyzing features of the anterior eye part images.

The image processing unit 305 performs binarization processing on an anterior eye part image with a predetermined threshold, and detects a pupil area. The image processing unit 305 then calculates a position of the center of gravity of the detected pupil area. The image processing unit 305 calculates the positional deviation amounts in the X and Y directions from a difference between the position of the calculated center of gravity of the pupil area and a predetermined position in the anterior eye part image. Here, the positional deviation amounts in the X and Y directions may be calculated from at least either one or both of the anterior eye part images obtained by the stereoscopic cameras 180-1 and 180-2.

The image processing unit 305 calculates a difference between the position of the center of gravity of the pupil area calculated from the anterior eye part image of the stereoscopic camera 180-1 and that calculated from the anterior eye part image of the stereoscopic camera 180-2. The image processing unit 305 then calculates the positional deviation amount and direction in the Z direction from the difference (parallax) between the positions of the centers of gravity, the distance between the stereoscopic cameras 180-1 and 180-2, and the focal length, using the principle of triangulation.

While the center of gravity of the pupil area is used as the features of the anterior eye part images, the position deviation amounts may be calculated based on a pupil center position. An index may be projected on the cornea, and the positional deviation amounts may be calculated based on the index. The anterior eye part may be observed with a split prism inserted in the observation optical system.

<Methods for Adjustment Operations>

Methods for adjustment operations according to the present exemplary embodiment will be described. The ophthalmic apparatus according to the present exemplary embodiment performs an alignment adjustment that is one of the adjustment operations, a focus adjustment that is one of the adjustment operations, and a coherence gate adjustment that is one of the adjustment operations. The adjustment operations may include any adjustment for the sake of an inspection, and are not limited to the foregoing three. For example, a polarization operation for optimizing OCT output sensitivity may be performed.

The method for the alignment adjustment that is one of the operations for adjusting the optical head unit 100 with respect to the eye E to be inspected will initially be described.

The imaging control unit 301 issues a movement instruction to the head driving unit 170 to reduce the positional deviation amounts calculated by the image processing unit 305. The head driving unit 170 then drives the three not-illustrated motors to move the position of the optical head unit 100 with respect to the eye E to be inspected in the three-dimensional (X, Y, and Z) directions.

After the movement of the optical head unit 100, the image processing unit 305 obtains the anterior eye part images and detects the pupil area again. The image processing unit 305 determines whether the pupil of the eye E to be inspected has been moved into a specified range set in advance on the display screen. In a case where the pupil is determined to have been move into the specified range, the alignment adjustment ends. On the other hand, in a case where the pupil of the eye E to be inspected does not fall within the specified range, the foregoing processing is repeated.

Alternatively, a split prism may be inserted into the observation optical system and the positional deviation amounts may be calculated based on split anterior eye part images. An alignment index may be projected on the anterior eye part, and the optical head unit 100 may be moved based on the position where the index is projected. A plurality of alignment indexes including rough and fine alignment indexes may be used to perform a rough adjustment and a fine adjustment step by step. A plurality of such alignment adjustment methods may be performed in combination.

Next, the focus adjustment for the fundus part of the eye E to be inspected, which is one of the adjustment operations according to the present exemplary embodiment, will be described.

The image processing unit 305 obtains a fundus image and calculates contrast of the obtained fundus image. The imaging control unit 301 moves the focus lens 133 to obtain the fundus image having high contrast. After the movement of the focus lens 133, the image processing unit 305 obtains a fundus image and calculates the contrast again. In a case where the contrast reaches or exceeds a reference level set in advance, the focus adjustment ends. On the other hand, in a case where the contrast falls below the reference level, the foregoing processing is repeated.

The fundus image for the focus adjustment may be one obtained by any fundus imaging technique, such as an infrared fundus image and an SLO (confocal laser scanning method using a near infrared light source) image. A method for calculating the brightness of the entire fundus image or a method for converting the fundus image into frequencies may be used aside from the contrast.

The focus adjustment may be performed by using other methods. For example, a sensor for detecting a phase difference in an image may be provided, and the optical head unit 100 is moved based on the phase difference (phase difference autofocusing). The imaging pixels may be configured to have the phase detection function. A slit and a split prism may be inserted into the optical path, and the focus lens 133 may be moved in such a way that the split light beams converge again. In the case of OCT imaging, the luminance and position of the two-dimensional tomographic image (OCT image) obtained by the OCT imaging may be detected and the lens 154 for focus adjustment may be moved in such a way that the luminance and position fall within appropriate ranges. A plurality of operations described above may be performed in combination as a focus adjustment.

In the case of OCT imaging, the coherence gate adjustment that is one of the adjustment operations is further performed. The image processing unit 305 obtains an OCT image and detects the position of the tomographic image. Based on the position of the tomographic image, the imaging control unit 301 drives the reference mirror 160 to adjust the optical path length of the reference light. After the adjustment of the optical length, the image processing unit 305 obtains an OCT image again and detects the position of the tomographic image. In a case where the tomographic image falls within an area set in advance, the coherence gate adjustment ends. In a case where the tomographic image does not fall within the area, the foregoing processing is repeated. In the coherence gate adjustment, instead of changing the optical length of the reference light, a mirror may be inserted into the optical path of the measurement light and the optical path length of the measurement light may be changed by changing the mirror position.

The foregoing adjustment operations may be performed in different order or at the same time. For example, when the rough alignment adjustment ends, the fine alignment adjustment and the focus adjustment may be started at the same time. After the end of the adjustment operations for the alignment adjustment, the focus adjustment, and the coherence gate adjustment, fine adjustments may be performed by performing the adjustment operations for the alignment adjustment, the focus adjustment, and the coherence gate adjustment again.

<Operation Procedure for Series of Inspections Based on Inspection Protocol>

Figure 3:
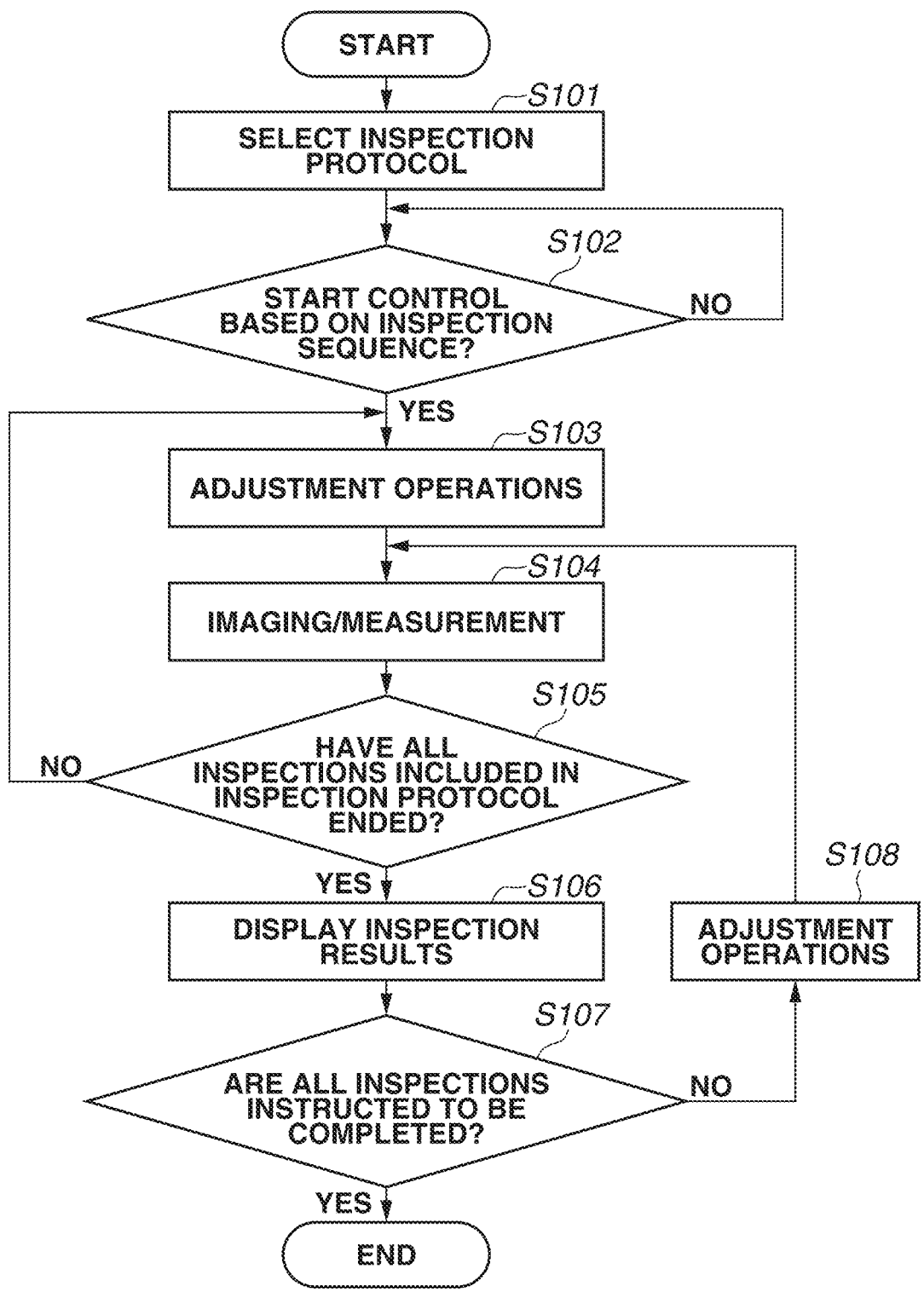
FIG. 3 is a flowchart illustrating an example of a measurement procedure according to the first exemplary embodiment.
Figure 4:
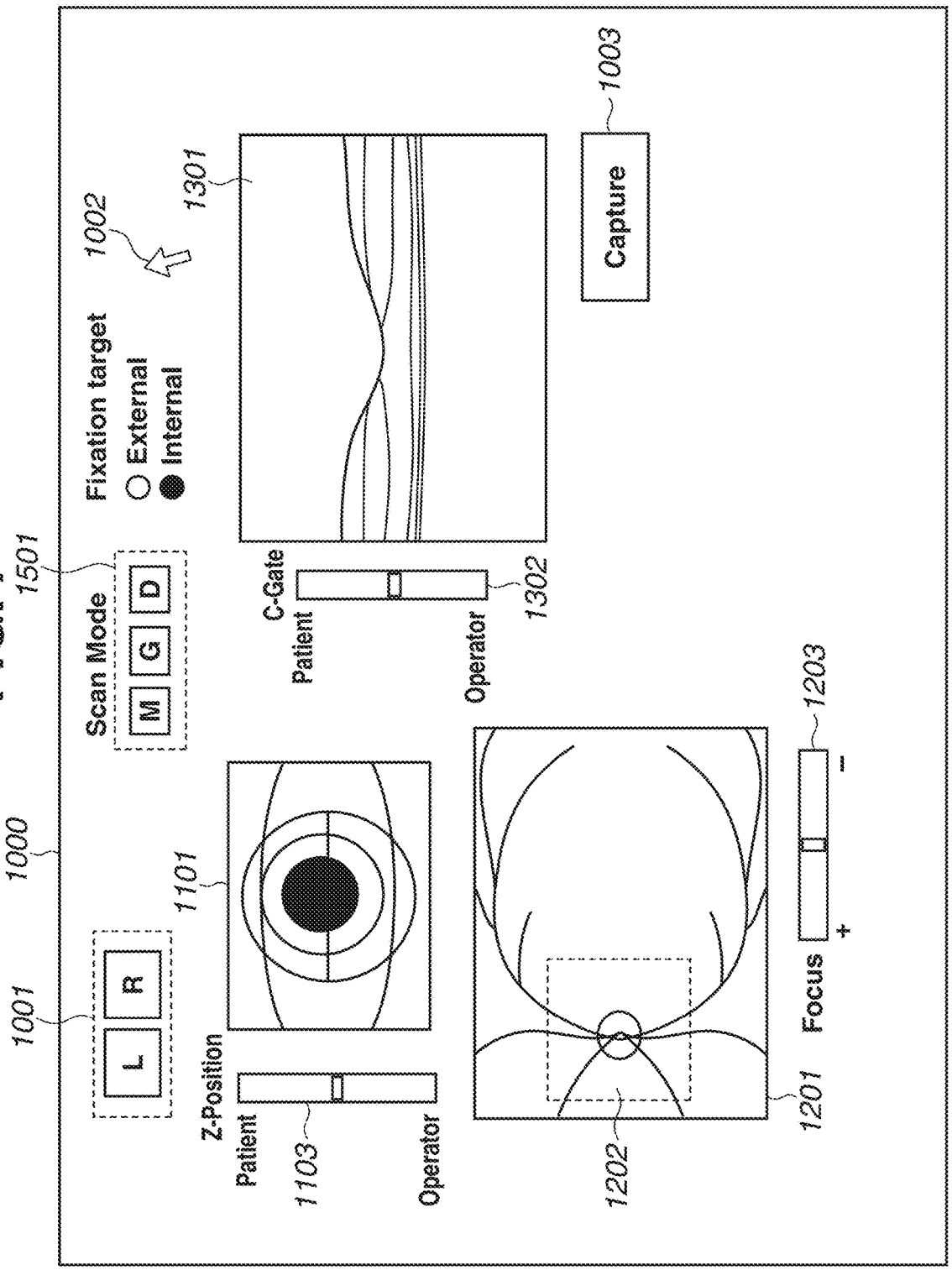
FIG. 4 is a diagram illustrating an example of an imaging screen according to the first exemplary embodiment.

An operation procedure for a series of inspections based on an inspection protocol according to the present exemplary embodiment will be described with reference to FIGS. 3 and 4. Here, a case where OCT imaging is first performed and visible light fundus imaging is then performed will be described as an example of the inspection protocol.

Before imaging, in step S101, the selection unit for selecting an inspection protocol selects an inspection protocol based on user instructions. The selection unit for selecting an inspection protocol may be included in the control unit 300. The inspection protocol selection screen displays a plurality of inspection protocols stored in the storage unit 302 in advance. Each inspection protocol defines a series of control procedures for performing a plurality of inspections including an alignment adjustment.

The user may input instructions by tapping on display information capable of identifying the inspection protocols on the not-illustrated inspection protocol selection screen displayed on the display unit 310. In displaying the display information capable of identifying the inspection protocols, the names of the inspection protocols may be displayed. Imaging icons graphically representing the imaging conditions defined for the inspection protocols may be displayed.

An inspection protocol may include information about imaging conditions, such as an imaging mode, a scan mode, and whether the eye E to be inspected is the left eye or the right eye. The order and the numbers of times of a plurality of inspections can be set by the user in advance. The set order and numbers of times are stored in the storage unit 302. For example, an inspection protocol can be selected or set to inspect both the left and right eyes in succession. The imaging to display the inspection result of on the display unit 310 after the end of the inspections can be selected and set from among the inspections included in the inspection protocol except for the last inspection. For example, in executing control based on an inspection protocol for performing OCT imaging and fundus imaging, an OCT image can be displayed on the display unit 310 after the end of the OCT imaging, followed by the fundus imaging.

Possible imaging modes include a fundus imaging mode, a fundus fluorographic imaging mode, an OCT imaging mode, and an anterior eye part imaging mode. Possible scan modes include a macular mode, a glaucoma mode, a disc mode, and an OCT angiography (OCTA) mode. In a case where the scan mode is switched, a scanning pattern and a fixation position optimum for the scan mode are set. Possible OCT scan patterns include three-dimensional (3D) scanning, radial scanning, cross scanning, circular scanning, and raster scanning.

Among a plurality of different inspection protocols, some inspection protocols may include imaging operations of the same imaging mode but different in scan modes or may include an additional imaging condition(s). An example of a plurality of difference inspection protocols stored in the storage unit 302 is an inspection protocol for performing OCT 3D scanning and fundus imaging and an inspection protocol for performing OCT radial scanning and fundus imaging. In the present exemplary embodiment, a case of selecting 3D scanning from among the OCT scanning patterns and performing fundus imaging as well will be described.

In step S102, the not-illustrated inspection protocol selection screen transitions to an imaging screen 1000 that is an example of a first screen, and the image obtaining unit 304 starts to obtain an anterior eye observation image. Here, an anterior eye observation image 1101, a fundus observation image 1201, and a tomographic image 1301 are displayed on the imaging screen 1000 of FIG. 4 on the display unit 310. Before imaging is started, moving images are displayed as the respective images 1101, 1201, and 1301.

The anterior eye observation image 1101 displayed may be an image corrected as if the anterior eye part Ea is seen from the front, not obliquely. Either one or both of the anterior eye part images obtained by the stereoscopic cameras 180-1 and 180-2 may be displayed as the anterior eye observation image 1101.

The imaging screen 1000, an example of the first screen, does not need to simultaneously display the anterior eye observation image 1101, the fundus observation image 1201, and the tomographic image 1301. For example, only the anterior eye observation image 1101 may be displayed while the user is adjusting the chin cup. The windows for displaying the fundus observation image 1201 and the tomographic image 1301 may be blacked out or display static until the images are obtained.

The imaging screen 1000, an example of the first screen, may include a plurality of screens to be switched based on the progress of the adjustment of the chin cup and the adjustment operations. For example, only the anterior eye observation image 1101 may be displayed while the user is adjusting the chin cup and while the alignment adjustment is performed. The fundus observation image 1201 and the tomographic image 1301 may be displayed while the focus adjustment or the coherence gate adjustment is performed.

In a case where the user taps on a capture button 1003 on the imaging screen 1000 that is an example of the first screen (YES in step S102), the processing proceeds to step S103 to start control based on the inspection protocol. While the operation on the capture button 1003, which is an example of the user instructions, is described as a predetermined condition to start the control based on the inspection protocol, the predetermined condition is not limited thereto. For example, the control based on the inspection protocol may be started by using an output of a contactless sensor for detecting approach of the examinee to the ophthalmic apparatus or a contact sensor for detecting placement of the examinee's chin on the chip cup as the condition.

In step S103, the alignment adjustment that is one of the adjustment operations is performed. The imaging control unit 301 issues instructions to the head driving unit 170 to reduce the position deviation amounts calculated by the image processing unit 305. The head driving unit 170 then drives the three not-illustrated motors to move the position of the optical head unit 100 with respect to the eye E to be inspected in the three-dimensional (X, Y, and Z) directions. In this operation, the eye E to be inspected is illuminated with the infrared rays from the anterior eye part observation light source 125. When the alignment adjustment is completed, the final alignment positions for the respective types of imaging are stored in the storage unit 302.

Next, the focus adjustment that is one of the adjustment operations is performed. The image processing unit 305 obtains a fundus image and calculates contrast of the obtained fundus image. The imaging control unit 301 moves the focus lens 133 in such a way that the contrast of the fundus image increases.

Then, the coherence gate adjustment that is one of the adjustment operations is performed. The image processing unit 305 obtains an OCT image and detects the position of the tomographic image. Based on the position of the tomographic image, the imaging control unit 301 drives the reference mirror 160 to adjust the optical path length of the reference light.

The adjustment operations in step S103 may be performed in different order or at the same time. For example, after the end of the rough alignment adjustment, the fine alignment adjustment and the focus adjustment may be started at the same time. After the end of the adjustment operations for the alignment adjustment, the focus adjustment, and the coherence gate adjustment, fine adjustments may be performed by performing the adjustment operations for the alignment adjustment, the focus adjustment, and the coherence gate adjustment again.

The ophthalmic apparatus may have a function where the user manually adjusts the focus and the alignment without using the foregoing automatic imaging functions. The user moves the position of the optical head unit 100 with respect to the eye E to be inspected in the Z direction by using a slider 1103. The user also performs a focus adjustment by using a slider 1203, and performs a coherence gate adjustment to the tomographic image 1301 by using a slider 1302. The user adjusts the scan range displayed on the fundus observation image 1201. The user then taps on the capture button 1003 to capture images. While the capture button 1003 serves as a button for accepting an instruction to perform the adjustment operations in the case of the automatic imaging, the capture button 1003 serves as a button for accepting an instruction to obtain images after completion of manual adjustments. In a case where the capture button 1003 is tapped, the imaging control unit 301 drives the OCT X and Y scanners 153-1 and 153-2 to perform a 3D scan.

The imaging screen 1000 may include or not include a stop button that is an example of display information for suspending the control based on the inspection protocol. The imaging screen 1000 may further include or not include a restart button that is an example of display information for resuming the control based on the inspection protocol if the control is suspended.

The imaging screen 1000, an example of the first screen, does not need to simultaneously display the anterior eye observation image 1101, the fundus observation image 1201, and the tomographic image 1301. The imaging screen 1000 may include a plurality of screens to be switched with the progress of the adjustment of the chin cup and the adjustment operations. For example, only the anterior eye observation image 1101 may be displayed while the user is adjusting the chin cup and while the alignment operation is performed. The fundus observation image 1201 and the tomographic image 1301 may be displayed while the focus adjustment or the coherence gate adjustment is performed.

In step S104, an image of the eye E to be inspected is captured. The image of the eye E to be inspected is stored into the storage unit 302. The image can be captured immediately after the end of the foregoing adjustment operations, or after a preset time has been counted down. The ophthalmic apparatus may have a function where the user can select one of such settings. While a description for the present exemplary embodiment will be given of a case of obtaining an image of the eye E to be captured as an example of the inspection, eye characteristics such as refractive power may be measured.

After the imaging or measurement is performed in step S104, the imaging control unit 301 serving as an example of the control unit moves the optical head unit 100 serving as an example of the inspection unit at a predetermined position. The position where the optical head unit 100 is put on standby is either the position of the optical head unit 100 at the end of the imaging or measurement or a position to which the optical head unit 100 is moved from the position at the end of the imaging or measurement in a direction away from the examinee in the Z direction.

Here, the position where the optical head unit 100 is put on standby does not need to be exactly the same as the position of the optical head unit 100 in the X and Y directions at the end of the imaging or measurement. The optical head unit 100 can be put on standby at a position within a certain range, to decrease the time for the alignment adjustment for the next inspection in comparison with the case where the optical head unit 100 is not put on standby but returned to an initial position of the optical head unit 100. Such a control method can be changed by a setting, and the optical head unit 100 may be moved to the initial position at power-on after the end of the imaging or measurement.

Since the optical head unit 100 is put on standby near the final alignment position after the end of the imaging or measurement, the time for the alignment adjustment for performing imaging or measurement instructed from a result screen to be described below can be reduced. To reduce burden on the examinee, the optical head unit 100 may be moved away from the examinee.

The imaging control unit 301 may be configured to, when switching the left and right eyes to conduct the next inspection, set the position of the optical head unit 100 to be moved in a lateral direction, not the foregoing front-to-back direction. When the last inspection is one on the right eye, the time to be taken for the next alignment adjustment can be reduced by putting the optical head unit 100 on standby at the position at the end of the inspection or at a position closer to the left eye. Conversely, when the last inspection is one on the left eye, the time to be taken for the next alignment adjustment can be reduced by putting the optical head unit 100 on standby at the position at the end of the inspection or at a position closer to the right eye.

During the standby, the state of continuously detecting the relative position information about the eye E to be inspected and the optical head unit 100 is maintained so that the ophthalmic apparatus can return to the adjustment operation and the imaging or measurement anytime. Moreover, the time for the alignment adjustment for performing the next inspection can be reduced by controlling the movement of the optical head unit 100 in such a way that the optical head unit 100 is set within a range where the relative position information about the eye E to be inspected and the optical head unit 100 can be detected.

An example of the range where the relative position information about the eye E to be inspected and the optical head unit 100 can be detected is a range where the image processing unit 305 can detect the anterior eye part images. The range where the image processing unit 305 can detect the anterior eye part images refers to where the anterior eye part Ea of the eye E to be inspected falls within the angles of view of the observation units. The anterior eye part Ea of the eye E to be inspected is desirably maintained within the angles of view of the observation units so that the next alignment adjustment is quickly performed.

In a case where the relative position information is determined to not be detectable by the observation units intended for the anterior eye part Ea of the eye E to be inspected, the audio output unit 350, an example of the notification unit, may issue a warning to the user. As another example, the display unit 310, an example of the display unit, may display a warning message. The head driving unit 170 may be driven in such a way that the anterior eye part Ea of the eye E to be inspected remains within the detection ranges of the observation units.

In step S105, the imaging control unit 301 determines whether all the inspections included in the inspection protocol selected in step S101 have ended. In a case where not all the inspection have ended (NO in step S105), the processing returns to step S103. The adjustment operations of step S103 and the imaging or measurement of step S104 are then performed. For example, in a case where the current control is based on an inspection protocol for performing OCT imaging and then fundus imaging, and only the OCT imaging has ended, the processing proceeds to the adjustment operations and imaging for the next fundus imaging. If all the inspections included in the selected inspection protocol have ended (YES in step S105), the processing proceeds to step S106 to display the inspection results.

Figure 5:
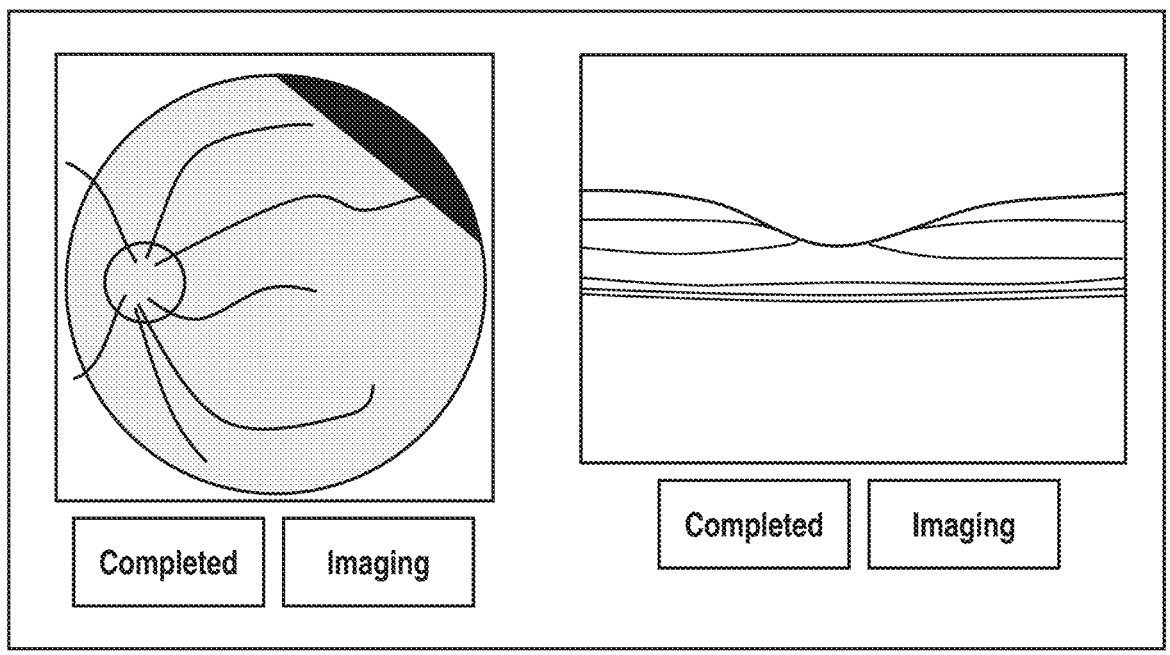
FIG. 5 is a diagram illustrating an example of a result screen according to the first exemplary embodiment.

In step S106, the imaging control unit 301 displays a result screen that is an example of a second screen. The result screen, an example of the second screen, includes the results of the inspections included in the inspection protocol selected in step S101 and imaging buttons that are examples of display information for accepting a reinspection instruction for some (a part) of a plurality of inspections. FIG. 5 illustrates an example of the result screen. The result screen displays an imaging button that is an example of the display information for accepting a reinspection instruction and a completion button that is an example of display information for accepting a completion instruction for each inspection, and thus either completion or imaging can be selected on the result screen. While, in FIG. 5, the display information for accepting a reinspection instruction is imaging buttons since an OCT image and a fundus image are displayed, a measurement button may be displayed as the display information for accepting a reinspection instruction in a case where the inspection protocol includes refractive power measurement.

Figure 6A:
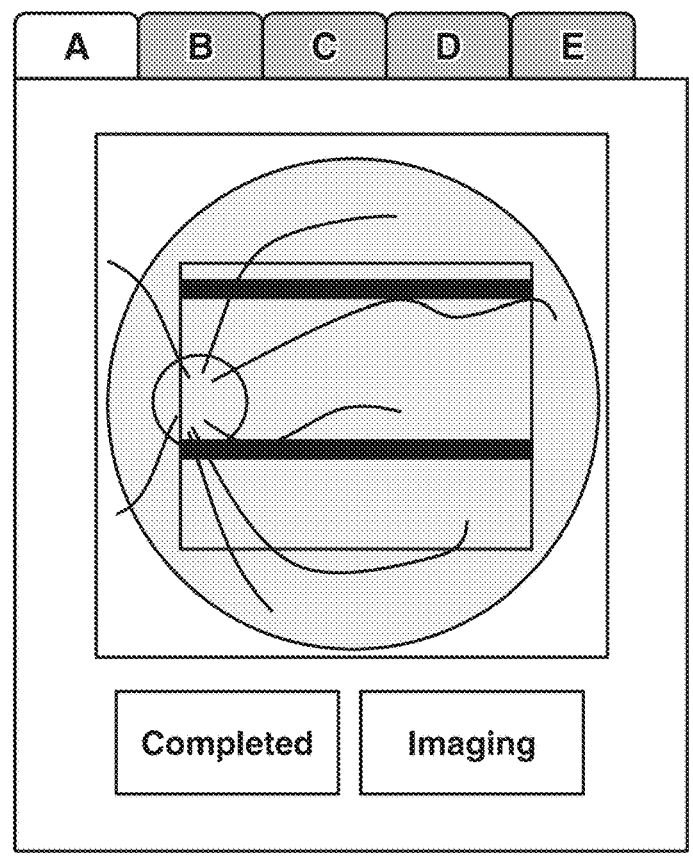
FIG. 6A is a diagram illustrating an example of a result screen including a plurality of screens according to the first exemplary embodiment.
Figure 6B:
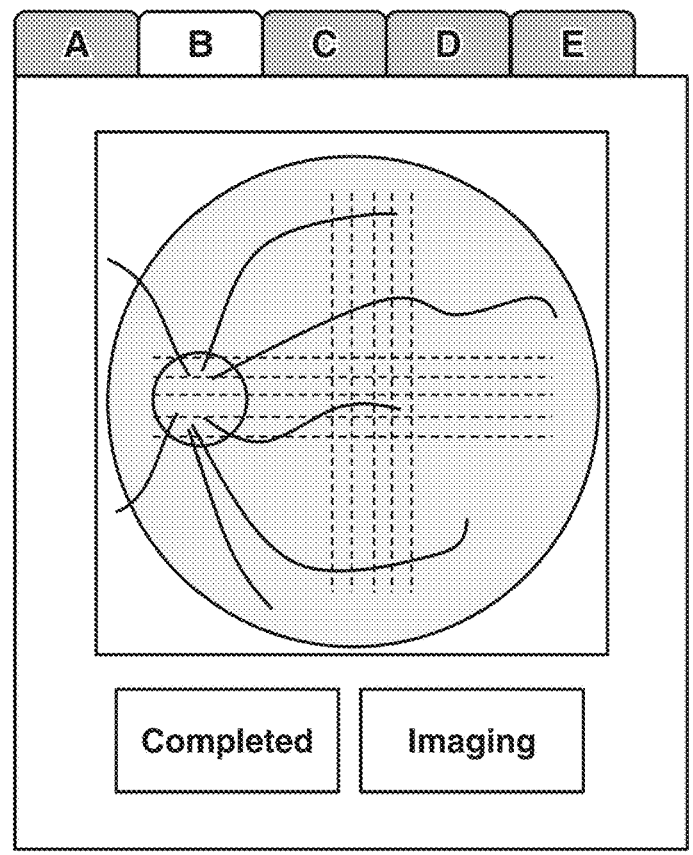
FIG. 6B is a diagram illustrating another example of a result screen including a plurality of screens according to the first exemplary embodiment.

The imaging buttons that are examples of the display information for accepting a reinspection instruction and the images are displayed in association with each other. The result screen may include a plurality of screens. For example, the screens may be switched with tabs. The inspection content may be displayed using icons, and a screen may be opened if an icon is tapped. The screens may be switched by swipe operations on the touch panel. FIGS. 6A and 6B illustrate examples of the result screens switchable with tabs. Alternatively, display times may be set for the respective screens, and the screens may be switched after a lapse of a predetermined time.

A screen may be generated for each inspection. When a reinspection instruction for an inspection is issued, the processing proceeds to either the step of performing the adjustment operations or the step of performing the imaging or measurement, and the result screen may be displayed again after the end of the inspection.

Figure 7:
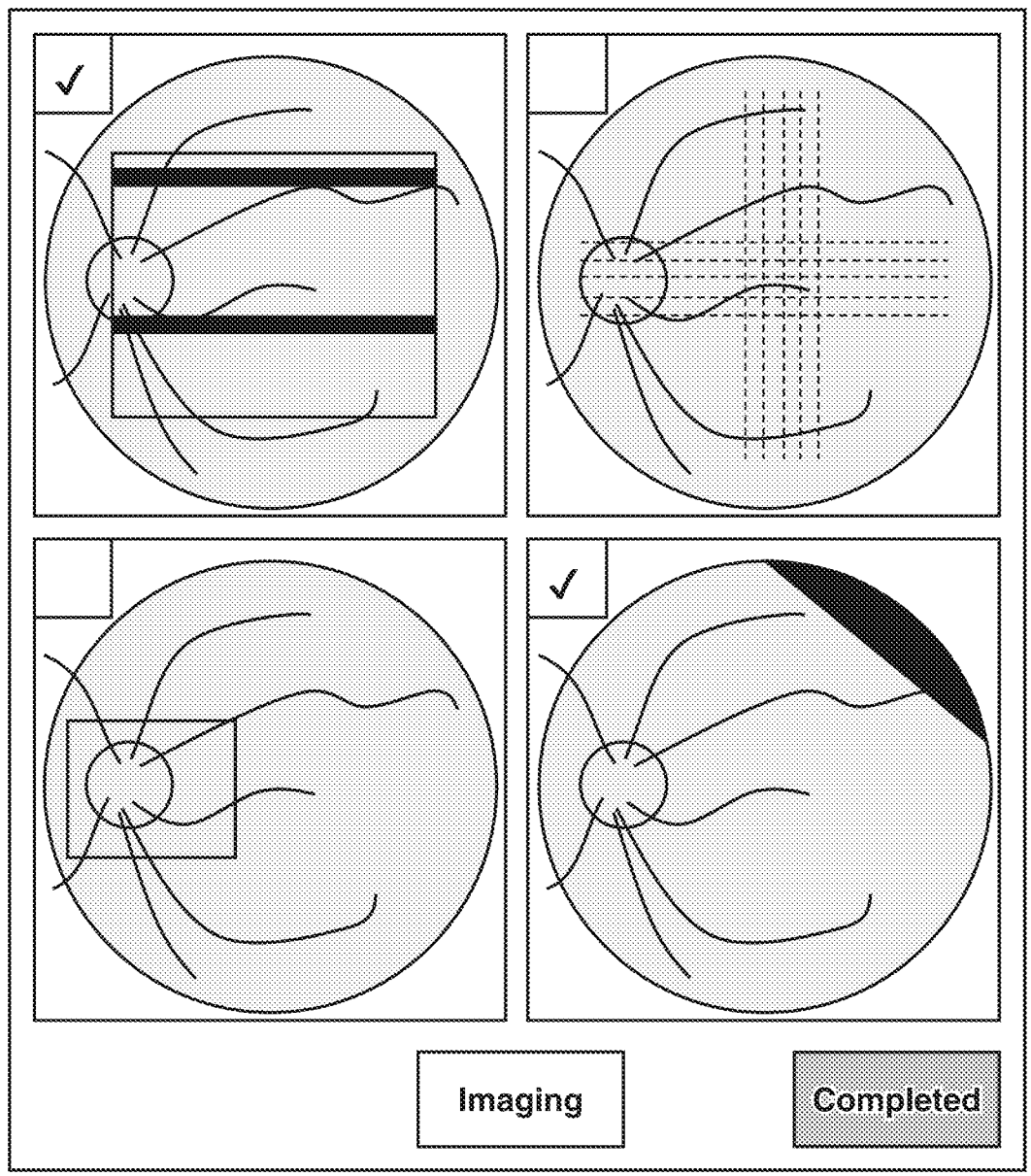
FIG. 7 is a diagram illustrating an example of a result screen according to the first exemplary embodiment.

The foregoing imaging and completion buttons may be in any form. The completion buttons do not need to be always displayed as long as all the inspections can be instructed to be completed. Checkboxes may be displayed in association with the respective images, along with a button for collectively performing checked imaging operations. FIG. 7 illustrates an example of the result screen including checkboxes. The result screen may be configured in such a way that completion or imaging can be selected by dragging and dropping icons or images corresponding to the inspections into a predetermined area.

The result screen may display determination criteria for the images, such as a numerical value indicating image quality, a status bar, a display indicating the position and degree of effect of flare or vignetting, and an image obtained by superimposing a line or frame indicating a scan position on a fundus front image. The result screen may include a function of reading a past inspection result of the examinee and displaying the past inspection result.

Figure 8A:
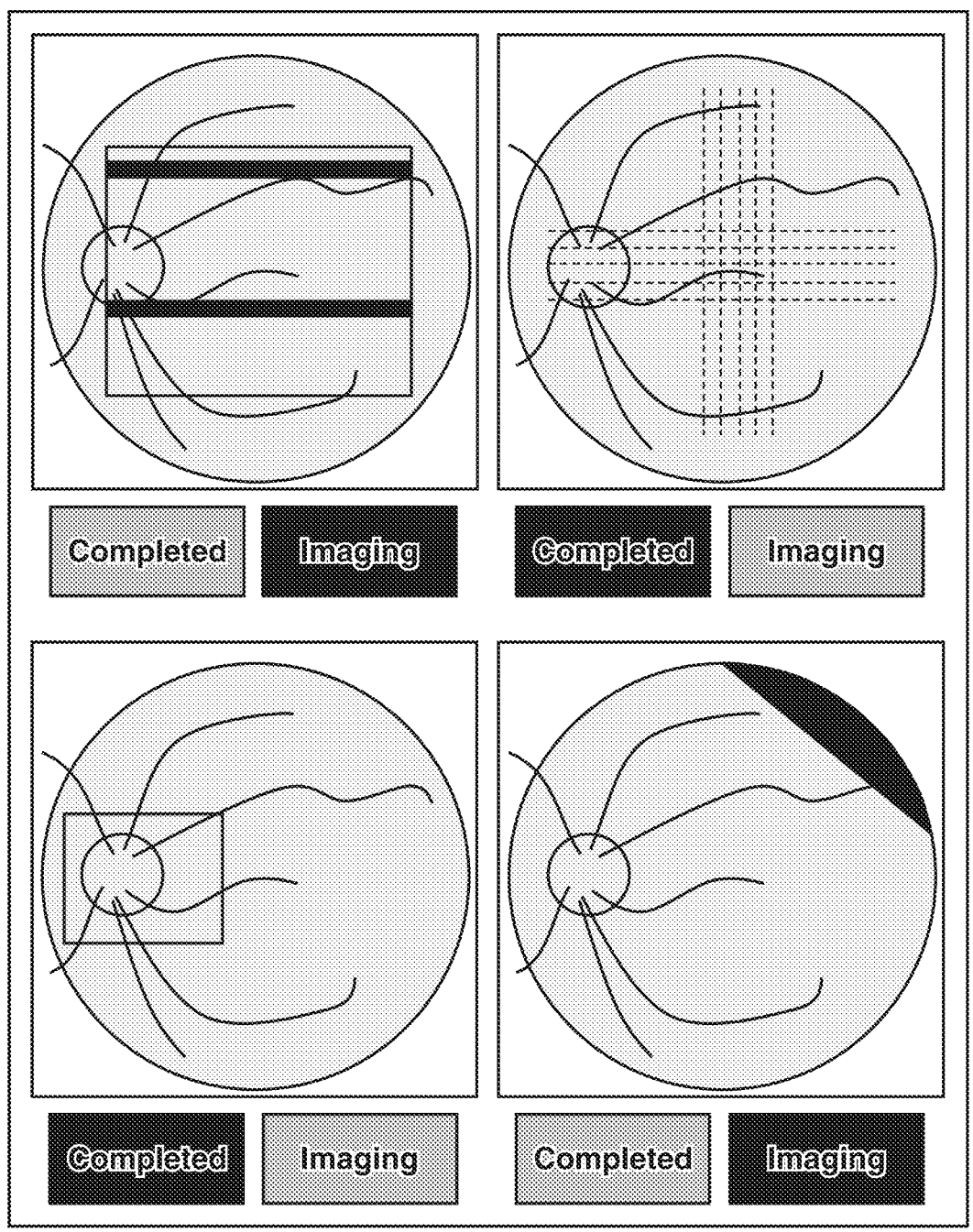
FIG. 8A is a diagram illustrating an example of a determination screen according to the first exemplary embodiment.
Figure 8B:
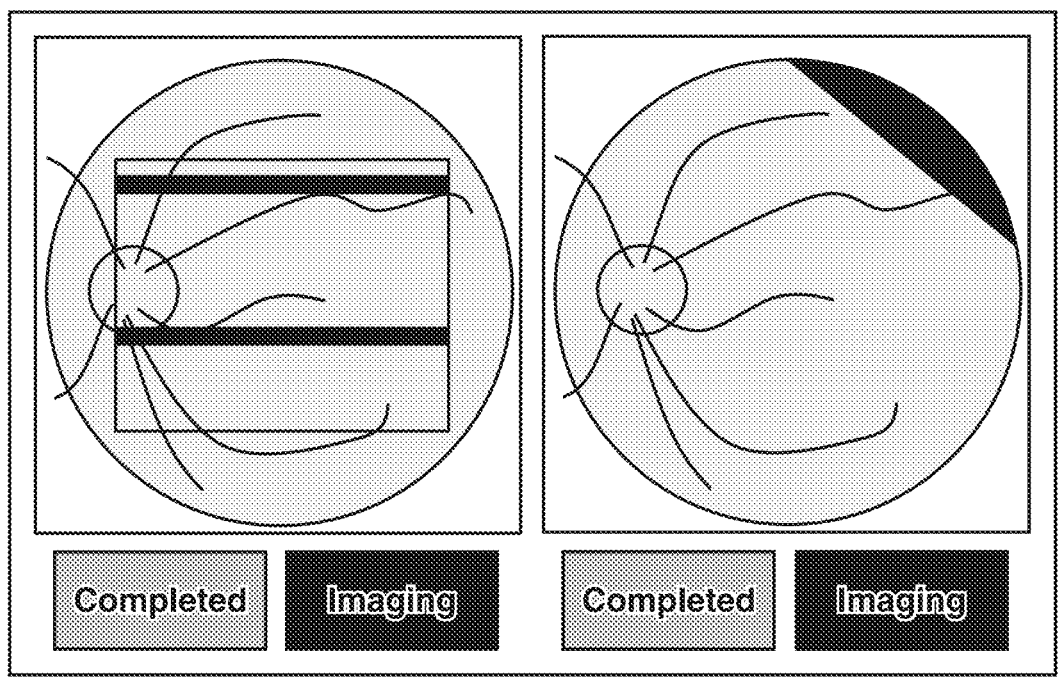
FIG. 8B is a diagram illustrating an example of a determination screen according to the first exemplary embodiment.

In step S107, the imaging control unit 301 determines whether all the inspections are instructed to be completed based on the state of acceptance of reinspection instructions in step S106. Here, the results of the inspections instructed and information about the inspections may be displayed on the display unit 310. FIG. 8A illustrates a determination screen where the instructions given for the respective inspections are displayed. FIG. 8B illustrates a determination screen where the results of the reinspection-instructed inspections are displayed. Alternatively, the results of the completed inspections may be grayed out for distinction. The determination screen does not necessarily need to be displayed. The processing may proceed to the inspection operations immediately after the acceptance of the user instructions in step S107. The ophthalmic apparatus may be configured to notify the user of information about the next inspection by voice guidance.

In step S107, in a case where all the inspections included in the selected inspection protocol are instructed to be completed (YES in step S107), the series of inspections ends. On the other hand, in a case where any reinspection instruction is given (NO in step S107), the processing proceeds to step S108 to perform the instructed inspection(s). Here, the already obtained result(s) of the instructed inspection(s) may be deleted from the storage unit 302 and only a new result or results obtained may be stored in the storage unit 302. Both the already obtained result(s) of the instructed inspection(s) and the result(s) obtained after the acceptance of the instruction(s) may be stored in the storage unit 302.

In step S108, the imaging control unit 301 performs the adjustment operations for performing the instructed inspection(s). Here, the optical head unit 100 may be driven to the final alignment position which is stored in the storage unit 302 in step S103. Starting the alignment adjustment from the stored alignment position can reduce the time for the alignment adjustment.

After the completion of step S108, the ophthalmic apparatus performs the reinspection-instructed inspection(s) and displays the result screen again. In performing the reinspection-instructed inspection(s), the ophthalmic apparatus according to the present exemplary embodiment performs the inspection(s) under the same inspection conditions as those of the inspections defined by the inspection protocol selected in step S101. During the inspection(s), the control unit 300 performs control based on the selected inspection protocol. In a case where all the inspections included in the selected inspection protocol are instructed to be completed, the series of inspections ends.

According to the ophthalmic apparatus of the exemplary embodiment, ophthalmic inspections can be smoothly conducted to improve the usability of the ophthalmic apparatus.

In a second exemplary embodiment, an ophthalmic apparatus that performs both OCT imaging and visible light fundus imaging will be described as an example of the ophthalmic apparatus according to an exemplary embodiment of the present invention. The ophthalmic apparatus according to the present exemplary embodiment stores inspection protocols each defining a series of control procedures including both OCT imaging and visible light fundus imaging, and the user can select one of the plurality of inspection protocols and issue an instruction to execute control based on the selected inspection protocol.

The ophthalmic apparatus according to the present exemplary embodiment includes a stop button 1004 and a restart button 1005. The stop button 1004 is an example of display information for accepting an instruction to suspend control based on the selected inspection protocol. The restart button 1005 is an example of display information for accepting an instruction to resume the control if the control is suspended. While the control based on the selected inspection protocol is performed, the user can tap on the stop button 1004 to suspend the operation. By tapping on the restart button 1005, the user can resume the control based on the selected inspection protocol without returning to the inspection protocol selection screen.

A configuration of the ophthalmic apparatus, a configuration of a control unit, a method for detecting relative position information, and methods for adjustment operations according to the second exemplary embodiment are similar to the configuration of the ophthalmic apparatus, the configuration of the control unit, the method for detecting the relative position information, and the methods for the adjustment operations according to the first exemplary embodiment. A redundant description thereof will thus be omitted.

<Operation Procedure for Series of Inspections Based on Inspection Protocol>

An operation procedure for a series of inspections based on an inspection protocol according to the present exemplary embodiment will be described with reference to FIGS. 9 and 10.

Steps S201, S202, and S203 are similar to steps S101, S102, and S103 according to the first exemplary embodiment, respectively. A description thereof will thus be omitted. The present exemplary embodiment differs from the first exemplary embodiment in that the stop button 1004, an example of the display information for accepting an instruction to suspend control, and the restart button 1005, an example of the display information for accepting an instruction to resume control, are displayed on the display unit 310 in step S204.

When the examinee moves unstably or when the user determines that the intended inspection is unable to be performed, the ophthalmic apparatus accepts an instruction to suspend the control based on the inspection protocol, to perform imaging under a favorable condition. When the condition becomes favorable, the ophthalmic apparatus can quickly perform the desired inspection by accepting an instruction to resume the control based on the inspection protocol without returning to the inspection protocol selection screen.

In step S204, the imaging control unit 301 determines whether to suspend the control based on the inspection protocol. In a case where the stop button 1004 is tapped by the user, the imaging control unit 301 determines to suspend the control based on the inspection protocol. While step S204 is illustrated to come between the adjustment operations and the imaging or measurement in FIG. 9, such processing order is not restrictive. The stop button 1004 may accept the user operation in any step between steps S202 and S205. In a case where the stop button 1004 is tapped (YES in step S204), the imaging control unit 301 suspends the control and the processing proceeds to step S206.

When the control is suspended, the user can input an instruction by tapping on the restart button 1005. In step S206, in a case where the restart button 1005 is tapped (YES in step S206), the imaging control unit 301 resumes the control based on the selected inspection protocol and the processing proceeds to step S203. Here, the inspection to be resumed is the one under the same inspection condition as that of the inspection performed before. In resuming the control, the imaging control unit 301 resumes the control from the adjustment operations or the imaging being performed when the control is suspended. In the case of performing measurement, the imaging control unit 301 similarly resumes the control from the adjustment operations or the measurement being performed when the control is suspended. For example, when the inspection protocol defines two imaging operations and the adjustment operations for the first imaging operation are being performed when the control is suspended, the imaging control unit 301 resumes the control from the adjustment operations for the first imaging operation.

The adjustment operations may be resumed from the suspended state. The adjustment operations may be resumed from a stage prior to where the adjustment operations are suspended. The imaging control unit 301 may be configured to return to a stage set by the user in advance and resume the control. Since the inspection protocol in progress is stored in the storage unit 302, the imaging control unit 301 can resume the control without returning to the inspection protocol selection screen.

When the optical head unit 100 is put on standby, the relative position information may be continuously detected as similar to the first exemplary embodiment. The ophthalmic apparatus may further include a notification unit so that the user can be notified of a warning when the relative position information is not detectable. The head driving unit 170 can be driven to maintain the eye E to be inspected within the detection range.

In FIG. 9, the processing ends after the imaging or measurement is performed in step S205. However, the procedure of steps S105 to S108 according to the first exemplary embodiment may be added to implement the first and second exemplary embodiments in combination.

According to the ophthalmic apparatus of the present exemplary embodiment, a suspended inspection can be resumed without returning to the inspection protocol selection screen. This improves the usability of the ophthalmic apparatus.

In the first and second exemplary embodiments, the ophthalmic apparatuses capable of performing OCT imaging and fundus imaging to obtain inspection results in the form of images have been described. However, the ophthalmic apparatuses may be configured to measure eye characteristics, such as refractive power.

While the ophthalmic apparatuses are described to include a control device (control unit) inside, the control unit capable of controlling the ophthalmic apparatuses may be disposed outside the ophthalmic apparatuses. Examples of such a control device include a personal computer and a tablet terminal.

Moreover, the control unit may include a plurality of control units. For example, one of the control units may display the inspection results on the display unit while another starts to control the optical units and the driving unit. Such a plurality of control units may be disposed inside the ophthalmic apparatus, or inside and outside the ophthalmic apparatus in a distributed manner.

In a third exemplary embodiment, a description will be given of an ophthalmic apparatus that puts an inspection on standby for a predetermined time based on previous and subsequent inspection content in an inspection protocol for performing a plurality of inspections. In such an ophthalmic apparatus, there can be a case where, when a plurality of inspections is automatically performed in succession, the time to be taken for the entire series of inspections is increased because each inspection processing is stopped more than appropriate before the start. There can also be a case where, inspections end up with an imaging failure because the inspections are unable to be stopped at arbitrary timing in the middle of the inspections. In view of this, the present exemplary embodiment is directed to efficiently performing successive inspections and obtaining stable inspection results. A configuration of the ophthalmic apparatus, a configuration of a control unit, a method for detecting relative position information, and methods for adjustment operations according to the third exemplary embodiment are similar to the configuration of the ophthalmic apparatus, the configuration of the control unit, the method for detecting the relative position information, and the methods for the adjustment operations according to the first exemplary embodiment. A redundant description thereof will thus be omitted. An operation procedure according to the present exemplary embodiment and the operation procedures described in the foregoing various exemplary embodiments may be performed in combination or in a substitutive manner at least in part without inconsistency.

An inspection operation procedure according to the present exemplary embodiment will be described with reference to FIGS. 12A to 12D and 13. Before the imaging, the user initially selects an inspection protocol on an inspection protocol selection screen (not illustrated) displayed on the display unit 310. The inspection protocol selection screen displays a plurality of inspection protocols stored in advance in the storage unit 302. Each of the plurality of inspection protocols defines a series of control procedures for executing a plurality of inspections including alignment adjustments. On the inspection protocol selection screen, imaging conditions, such as imaging modes, imaging parameters, and whether the eye E to be inspected is the left eye or the right eye, which are defined in an inspection protocol, the number of inspections, and the inspection order may also be selectable.

Figure 12A:
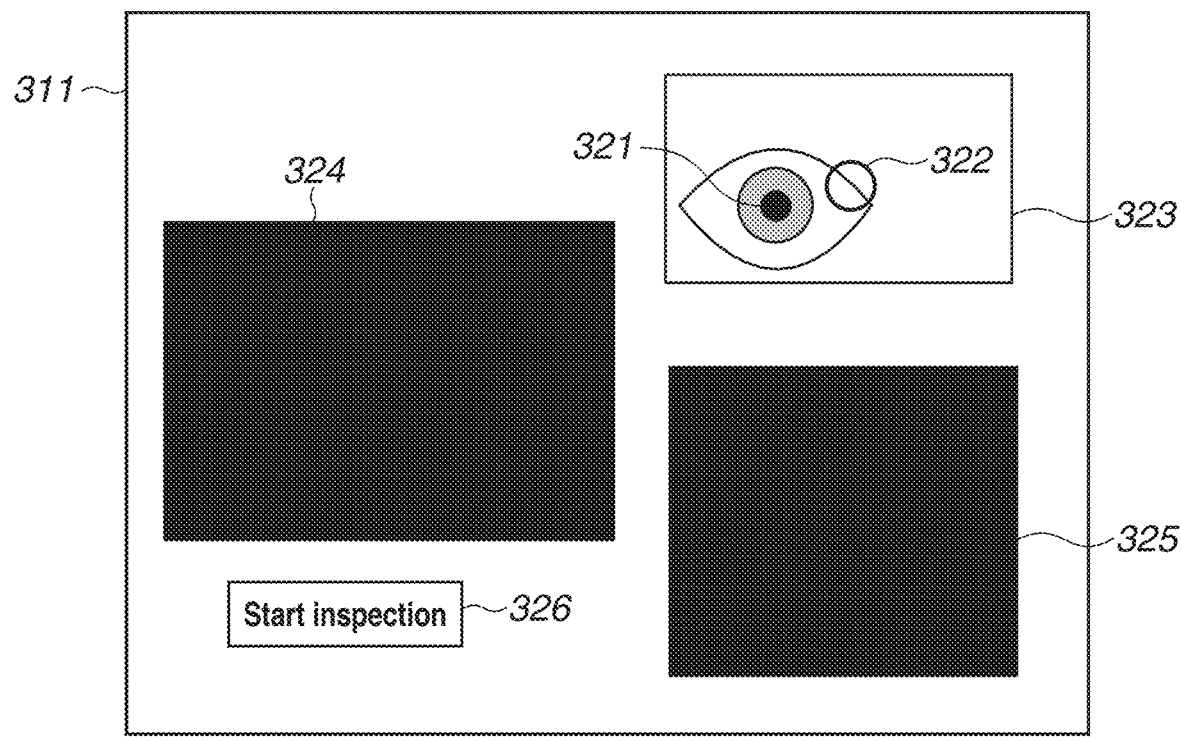
FIGS. 12A to 12D are diagrams each illustrating an example of screen display according to a third exemplary embodiment.

Next, the inspection protocol selection screen transitions to the imaging screen, and the image obtaining unit 304 starts to obtain anterior eye part images. Here, a screen 311 illustrated in FIG. 12A is displayed on the display unit 310. The screen 311 includes an anterior eye part image display area 323 (in this state, no anterior eye part image is displayed yet), a fundus image display area 324, and a tomographic image display area 325. The screen 311 includes an inspection start button 326 (start acceptance unit) for accepting an inspection start instruction. An anterior eye part moving image is displayed on the anterior eye part image display area 323 before a start of an inspection.

Next, the examinee is seated in front of the ophthalmic apparatus. In such a state, the user operates a not-illustrated operation unit to operate the head driving unit 170 capable of driving the optical head unit 100 in three-dimensional (X, Y, and Z) directions. Specifically, the user moves the optical head unit 100 to display a part of the pupil of the eye E to be inspected on the anterior eye part image display area 323. Here, the eye E to be inspected is illuminated with infrared rays from the anterior eye part observation light source 125.

After a part of the pupil of the eye E to be inspected is displayed on the anterior eye part image display area 323, the user presses the inspection start button 326 to start control based on the inspection protocol.

FIG. 13 is a flowchart of the control based on the inspection protocol that is performed by the imaging control unit 301. FIG. 13 illustrates an example of an inspection protocol for performing an inspection including tomographic imaging and an inspection including fundus imaging (first inspection) on the left eye of the examinee in order, and then performing an inspection including tomographic imaging (second inspection) and an inspection including fundus imaging on the right eye in order. Operations based on this inspection protocol will be described below.

In step S501, the imaging control unit 301 starts control based on the inspection protocol. The processing proceeds to step S502.

In step S502, the imaging control unit 301 aligns the optical head unit 100 with the left eye in the three-dimensional (X, Y, and Z) directions (alignment operation) by the foregoing method. After the completion of the alignment of the optical head unit 100, the processing proceeds to step S503.

Figure 12B:
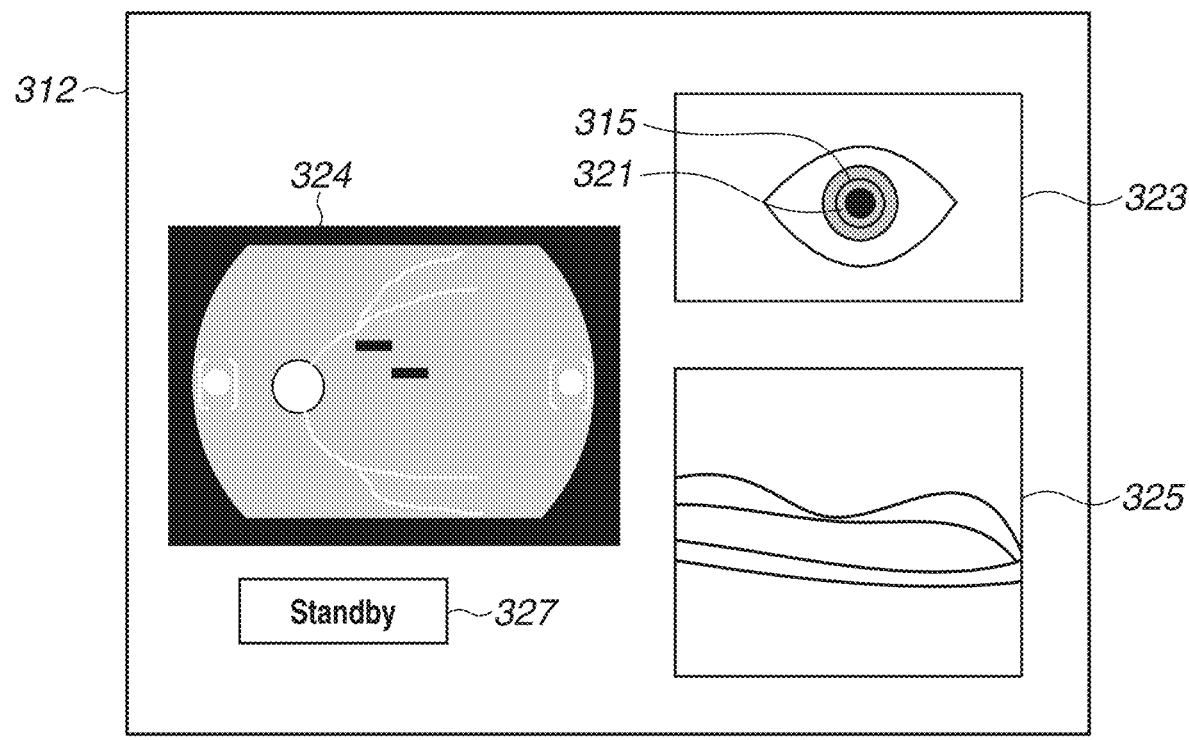

In step S503, the image obtaining unit 304 starts to obtain preview moving images for a fundus image and a tomographic image. Based on the obtained moving images, the imaging control unit 301 controls the components of the optical head unit 100 to perform imaging adjustments. The imaging adjustments here include a focus adjustment and an exposure adjustment for obtaining a fundus image, and a focus adjustment and an optical path length adjustment for obtaining a tomographic image. A screen 312 illustrated in FIG. 12B is displayed on the display unit 310. The screen 312 includes a standby button 327 (standby instruction acceptance unit). The fundus image display area 324 displays the fundus moving image, and the tomographic image display area 325 displays the tomographic moving image.

After the completion of the imaging adjustments, the processing proceeds to step S504.

In step S504, the imaging control unit 301 performs tomographic imaging using infrared rays under the imaging condition defined in the inspection protocol. After the completion of the imaging, the processing proceeds to step S505.

In step S505, the imaging control unit 301 performs fundus imaging using visible light under the imaging condition defined in the inspection protocol. Before the fundus imaging, the imaging control unit 301 may perform imaging adjustments again as appropriate. After the completion of the imaging, the processing proceeds to step S506.

In step S506, the imaging control unit 301 controls the head driving unit 170 to move the optical head unit 100 from in front of the left eye to in front of the right eye. The amount of movement here may be a predetermined fixed amount or an amount of movement based on past alignment results. After the completion of the movement, the processing proceeds to step S507.

In step S507, the imaging control unit 301 starts an alignment operation similar to that in step S502. When the pupil is successfully detected by the image processing unit 305, the processing proceeds to step S508. The ophthalmic apparatus may be configured to be operable by the user in this operation in a case where the pupil is not successfully detected.

Figure 12C:
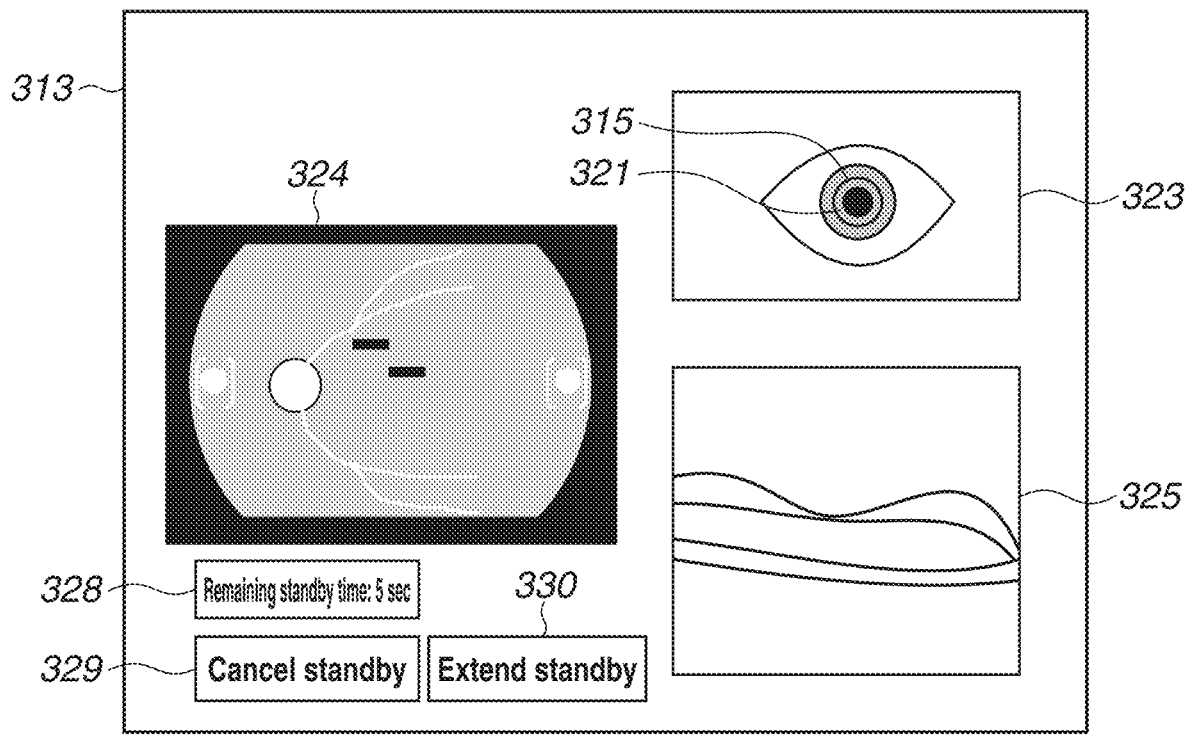
Figure 12D:
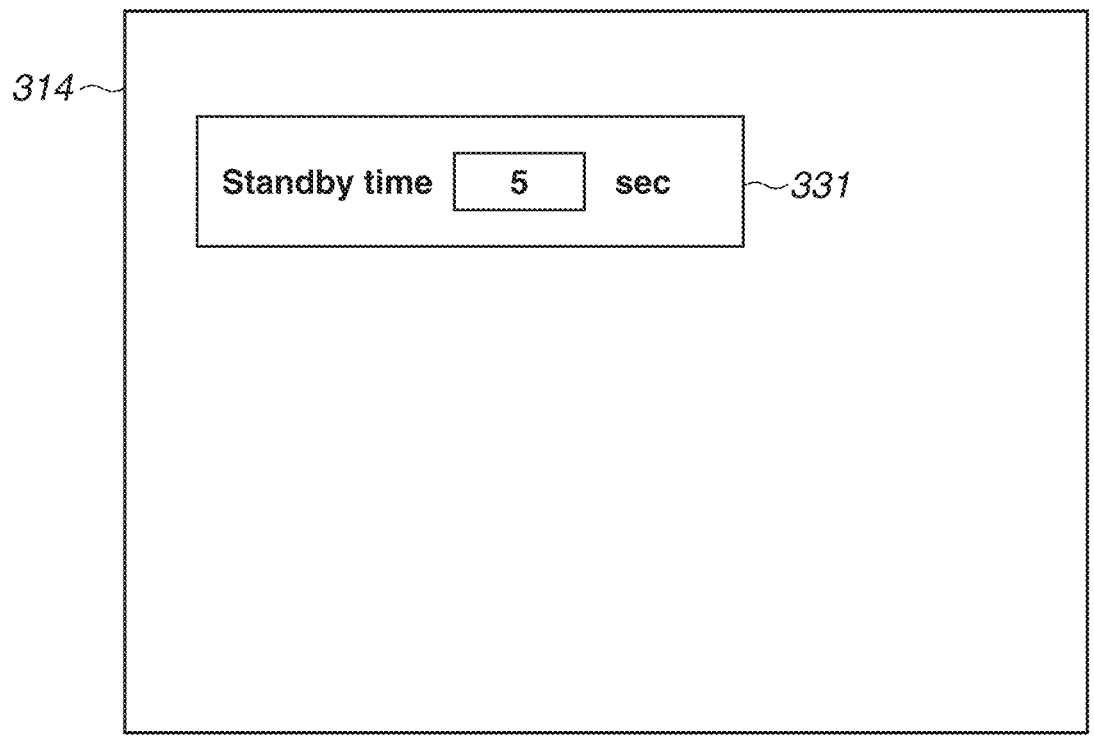

In step S508, the imaging control unit 301 suspends the inspection operation to dilate the pupil of the eye constricted due to the previous inspection using visible light. The following operations are performed during the standby: A screen 313 illustrated in FIG. 12C is displayed on the display unit 310. The screen 313 includes a remaining standby time display section 328, a standby cancellation button 329 (standby cancellation switch), and a standby extension button 330 (standby extension switch). If a condition to cancel standby to be described below is met, the processing proceeds to step S509.

In step S509, the imaging control unit 301 performs an alignment operation similar to that in step S502. After the completion of the alignment, the processing proceeds to step S510.

In steps S510 to S512, the imaging control unit 301 performs similar operations to those of steps S503 to S505.

In step S513, a not-illustrated imaging result check screen is displayed on the display unit 310. The inspection procedure ends.

In the inspection procedure of FIG. 13, the imaging operations are described to be immediately performed in steps S504, S505, S511, and S512. However, the images may be captured after a lapse of a predetermined time.

In the inspection procedure of FIG. 13, the alignment operations are described to be performed in steps S502, S507, and S509. However, the alignment operation with the left eye may be continued during steps S503 to S505. The alignment operation with the right eye may be continued during steps S510 to S512.

In the inspection procedure of FIG. 13, the inspection is described to be put on standby in step S508. However, the purpose of the standby is to temporarily suspend the execution of the imaging (steps S511 and S512). Step S508 for putting the inspection on standby can therefore be performed at any timing during the alignment operation and the imaging adjustments (steps S507 to S510).

<First Standby Operation Procedure During Standby>

The standby operation in step S508 that is performed in the inspection subsequent to the inspection using visible light will be described with reference to the flowchart of FIG. 14.

In step S601, the imaging control unit 301 suspends the inspection operation and starts standby. The processing proceeds to step S602. The imaging control unit 301 sets a standby time, and counts down the remaining time of the standby operation during steps S602 to S609. The output control unit 303 displays the remaining time in the remaining standby time display section 328 on the screen 313 illustrated in FIG. 12C. The output control unit 303 issues a notification of the remaining time by voice using the audio output unit 350.

In step S602, in a case where the imaging control unit 301 detects that the standby cancellation button 329 on the screen 313 illustrated in FIG. 12C is pressed (YES in step S602), the processing proceeds to step S610. In a case where the standby cancellation button 329 is not pressed (NO in step S602), the processing proceeds to step S603.

In step S603, in a case where the imaging control unit 301 detects that the standby extension button 330 on the screen 313 illustrated in FIG. 12C is pressed (YES in step S603), the processing proceeds to step S604. In a case where the standby extension button 330 is not pressed (NO in step S603), the processing proceeds to step S605.

In step S604, the imaging control unit 301 extends the remaining time of the standby operation by a predetermined time. The output control unit 303 updates the time in the remaining standby time display section 328 on the screen 313 illustrated in FIG. 12C. The processing proceeds to step S605. The remaining time here may be extended by a predetermined fixed value. The amount of the remaining time to be extended may be set individually. For example, the remaining time is increased by 5 sec each time the standby extension button 330 is pressed.

In step S605, the imaging control unit 301 determines whether the remaining time of the standby operation is 0 (whether the standby time has elapsed since the start of the standby). In a case where the remaining time of the standby operation is 0 (YES in step S605), the processing proceeds to step S610. In a case where the remaining time of the standby operation is not 0 (NO in step S605), the processing proceeds to step S606.

The standby time here is determined by the types or inspection parameters of the previous and subsequent inspections. The reason is that the state of pupil constriction varies depending on the previous inspection. For example, in a case where the amount of visible light used in the previous inspection is small, the pupil of the eye E to be inspected is less likely to constrict. The standby time can thus be determined based on the amount of visible light used in the previous inspection.

A minimum pupil diameter varies depending on the next inspection. For example, a minimum pupil diameter for fundus imaging is approximately 3.3 to 4.0 mm A minimum pupil diameter for tomographic imaging is 2.5 mm or so. The standby time can thus be determined based on the type of the next inspection.

The standby time can be reduced in a case where the amount of visible light used in the previous inspection is small and the minimum pupil diameter for the next inspection is small. The standby time may also be changed based on inspection parameters, such as the inspection mode and the number of images to be captured. The standby time may be determined based on a measurement result(s) obtained by measuring the pupil diameter at least either before or after an inspection.

The standby time here may be a numerical value prepared and stored in the storage unit 302 in advance, or one read from a conditional table stored in the storage unit 302. The standby time may be calculated using a calculation formula.

In step S606, the image processing unit 305 obtains anterior eye part images and performs the foregoing projective transformation on the anterior eye part images. The processing proceeds to step S607.

In step S607, the image processing unit 305 detects a pupil position (pupil position detection information) by the foregoing position information detection method. The processing proceeds to step S608.

In step S608, the image processing unit 305 determines whether the pupil position falls within a pupil detection range, based on the pupil position detection information. In a case where the pupil position is outside the pupil detection range (NO in step S608), the processing proceeds to step S609. In a case where the pupil position falls within the pupil detection range (YES in step S608), the processing proceeds to step S602. The pupil detection range here may be set to the same narrow range near the screen center as the range of the foregoing alignment method, and the alignment operation of step S507 may be continued even during the standby operation.

The pupil detection range may be set to as wide a range as possible on the anterior eye part image display area 323, and an alignment operation to not lose track of the pupil may be performed during the standby operation. With the wide alignment range, the optical head unit 100 is not moved much during the standby operation.

In step S609, the imaging control unit 301 controls the optical head unit 100 based on the pupil position detection information obtained in step S607 to set the pupil position within the pupil detection range determined in step S608. After the completion of the movement, the processing proceeds to step S602.

In step S610, the imaging control unit 301 cancels the standby operation and resumes the inspection operation.

In the present exemplary embodiment, the ophthalmic apparatus that puts an inspection in an inspection protocol for performing a plurality of inspections on standby for a predetermined time after an inspection using visible light, based on previous and subsequent inspection content has been described. In automatically performing a plurality of inspections in succession, each of the inspections have conventionally been stopped more than appropriate to wait until pupil constriction of the eye to be inspected is resolved. This can increase time for the entire series of inspections. In the present exemplary embodiment, the inspection is put on standby depending on the previous and subsequent inspection content. Since the inspections are suspended only as appropriate, stable inspection results can be obtained with high efficiency.

<Standby Button>

Next, a standby operation triggered by the standby button 327 on the screen 311 illustrated in FIG. 12B will be described. The standby button 327 can be pressed by the user anytime in the inspection procedure of steps S502 to S512 in FIG. 13. In a case where the standby button 327 is pressed, the imaging control unit 301 suspends the inspection operation and performs a standby operation including alignment operations similar to that of steps S602 to S609 in FIG. 14. The standby time here can be set by the user inputting or selecting a numerical value in a standby time setting section 331 (standby time setting unit) displayed on a setting screen 314 illustrated in FIG. 12D before the start of the inspections. A predetermined fixed value may be used.

During the standby operation, the screen 313 illustrated in FIG. 12C is displayed and the user can press the standby extension button 330 and the standby cancellation button 329. In a case where the standby extension button 330 is pressed, the remaining time of the standby operation is extended by a predetermined time as in steps S603 and S604. In a case where the standby cancellation button 329 is pressed, the standby operation is cancelled to resume the inspection operation.

In a case where the standby cancellation button 329 is pressed at timing after the imaging adjustments (step S503 or S510), the standby extension button 330 may be given a role as an imaging button for immediately capturing an image when pressed.

If a plurality of inspections is automatically performed in succession and the ophthalmic apparatus is unable to be stopped at an arbitrary timing during the inspections, the imaging can fail due to reasons such as a blink of the eye E to be inspected. In the present exemplary embodiment, stable inspection results can be obtained with high efficiency since the ophthalmic apparatus can be stopped at any timing.

An operation procedure according to a fourth exemplary embodiment is based on an inspection protocol for performing a plurality of inspections, where an inspection is put on standby for a predetermined time based on the measurement result of a pupil diameter. A configuration of an ophthalmic apparatus, a configuration of a control unit, a method for detecting relative position information, and methods for adjustment operations according to the fourth exemplary embodiment are similar to the configuration of the ophthalmic apparatus, the configuration of the control unit, the method for detecting relative position information, and the methods for the adjustment operations according to the first exemplary embodiment. A redundant description thereof will thus be omitted. The operation procedure according to the present exemplary embodiment and the operation procedures described in the foregoing various exemplary embodiments may be performed in combination or in a substitutive manner at least in part without inconsistency.

<Method for Measuring Pupil Diameter>

A description will be give of a method by which the image processing unit 305 according to the present exemplary embodiment measures a pupil diameter.

Like the method described in conjunction with the operation procedure of the third exemplary embodiment, the image processing unit 305 obtains anterior eye part images, performs projective transformation on the anterior eye part images, and detects a pupil area. The image processing unit 305 then makes an elliptical approximation of boundary coordinates of the pupil area, and measures the length of the minor axis (minor diameter) as a pupil diameter.

<Operation Procedure>

The operation procedure for inspections according to the present exemplary embodiment is based on an inspection protocol similar to that of the operation procedure for inspections according to the third exemplary embodiment (FIG. 13). A redundant description of the inspection protocol will thus be omitted.

<Second Standby Operation Procedure During Standby>

Figure 15:
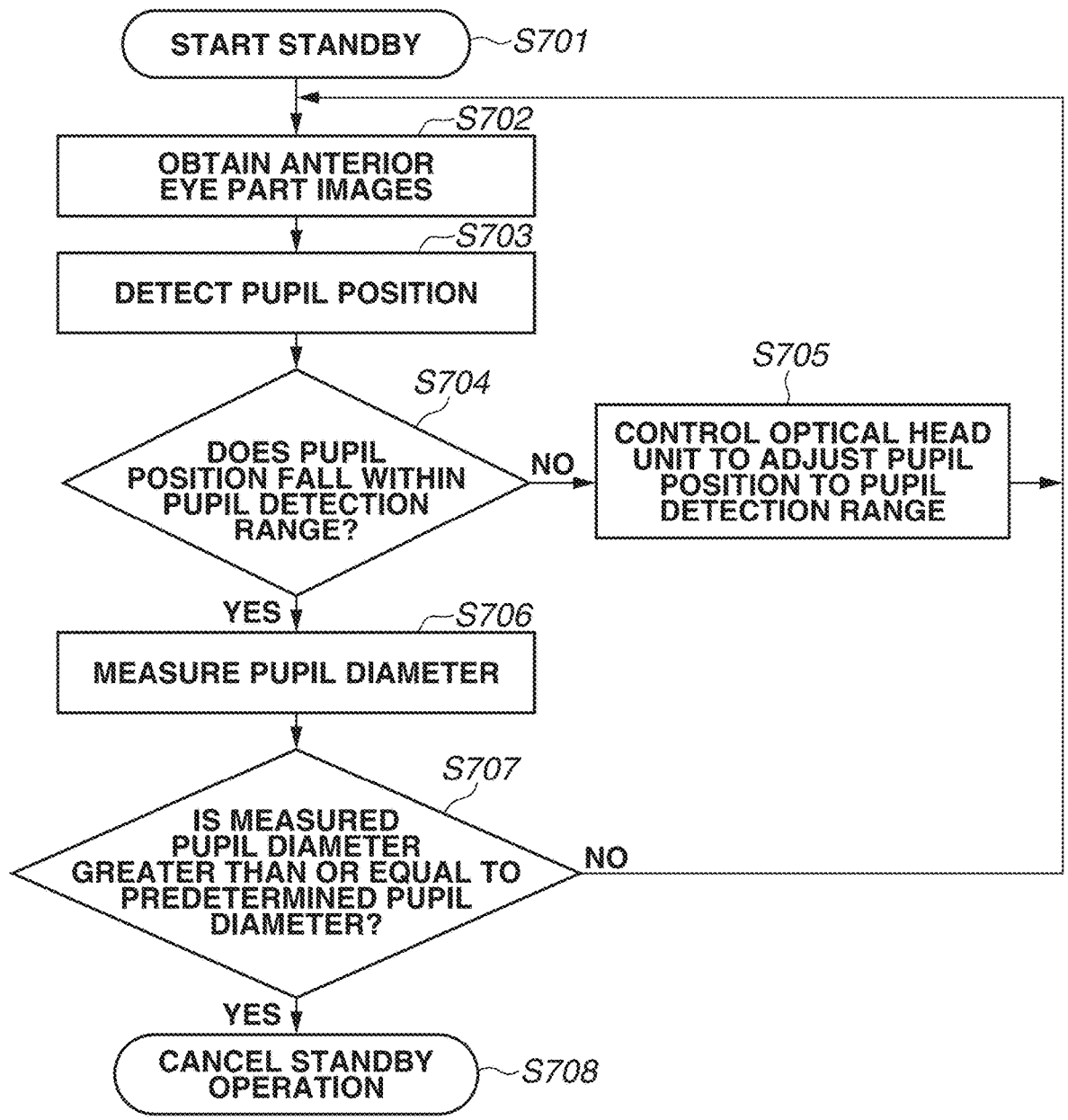
FIG. 15 is a flowchart illustrating an example of a second standby operation according to a fourth exemplary embodiment.

The standby operation of step S508 that is performed in an inspection subsequent to an inspection using visible light in the operation procedure will be described with reference to the flowchart of FIG. 15.

In step S701, the imaging control unit 301 suspends the inspection operation and starts a standby operation. The processing proceeds to step S702. The imaging control unit 301 sets the standby time, and counts down the remaining time of the standby operation during steps S702 to S707. The output control unit 303 displays the remaining time in the remaining standby time display section 328 on the screen 313 illustrated in FIG. 12C. The output control unit 303 issues a notification of the remaining time by voice using the audio output unit 350.

Figure 14:
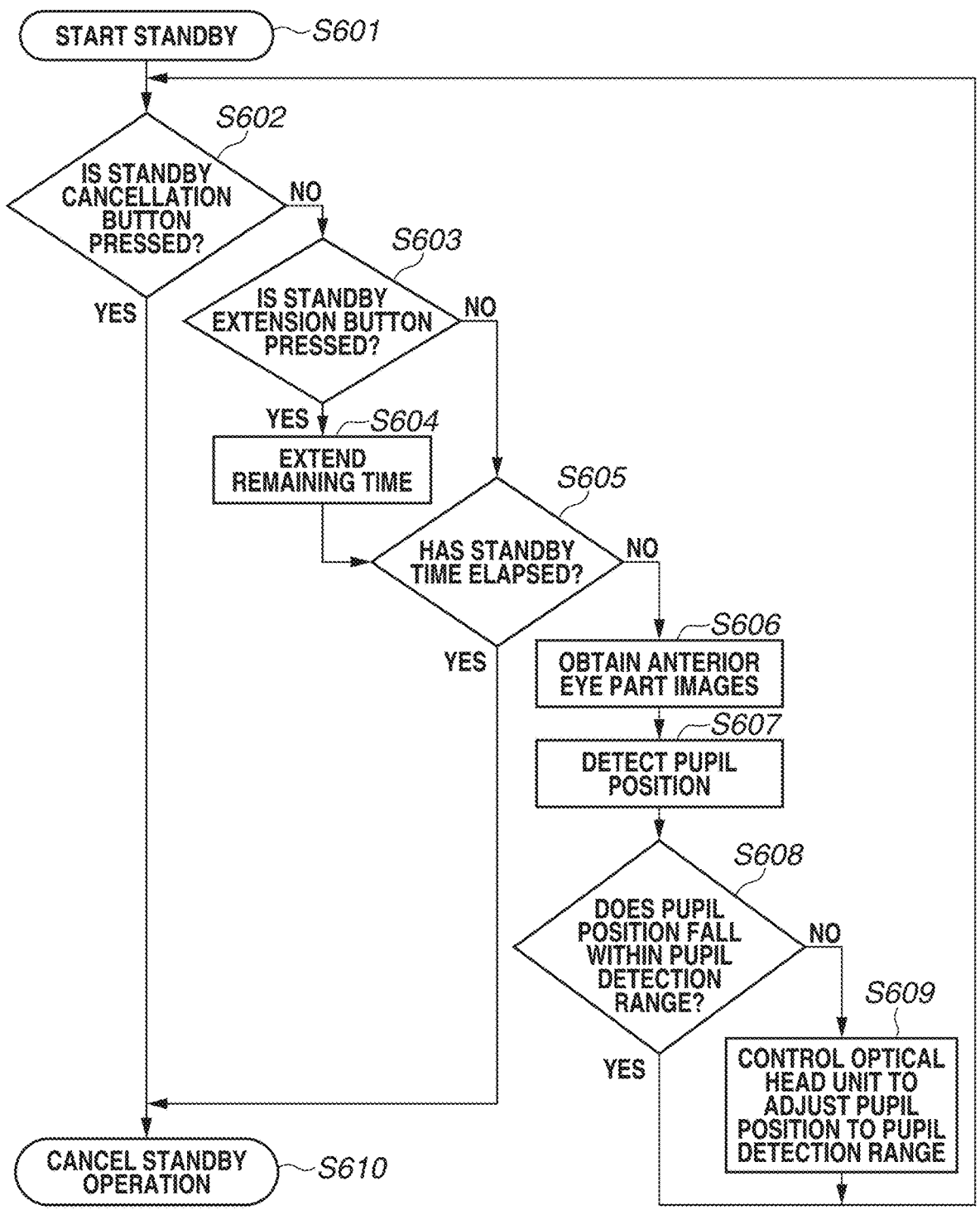
FIG. 14 is a flowchart illustrating an example of a first standby operation according to the third exemplary embodiment.

In steps S702 to S705, like steps S606 to S609 of FIG. 14, the imaging control unit 301 detects the pupil position from the anterior eye part images, determines whether the pupil position falls within the pupil detection range, and performs an alignment operation as appropriate.

In step S704, in a case where the detected pupil position falls within the pupil detection range (YES in step S704), the processing proceeds to step S706.

In step S706, the imaging control unit 301 measures the pupil diameter (pupil diameter measurement information) by the foregoing pupil diameter measurement method. The processing proceeds to step S707.

In step S707, the image processing unit 305 determines whether the measured pupil diameter is greater than or equal to a predetermined pupil diameter, based on the pupil diameter measurement information. In a case where the measured pupil diameter is smaller than the predetermined pupil diameter (NO in step S707), the processing returns to step S702. In a case where the measured pupil diameter is greater than or equal to the predetermined pupil diameter (YES in step S707), the processing proceeds to step S708. The determination criterion for the pupil diameter here is determined based on the type of the next inspection and the minimum pupil diameter desirable for the next inspection.

In step S708, the imaging control unit 301 cancels the standby operation and resumes the inspection operation.

In this operation procedure, the ophthalmic apparatus that puts an inspection in an inspection protocol for performing a plurality of inspections on standby for a predetermined time after an inspection using visible light, based on the measurement result of the pupil diameter, has been described. In automatically performing a plurality of inspections in succession, each of the inspections have conventionally been stopped more than appropriate to wait until pupil constriction of the eye to be inspected is resolved. This can increase time for the entire series of inspections. In the present operation procedure, since the inspection is put on standby depending on the measurement result of the pupil diameter, the inspections are suspended only as appropriate, whereby stable inspection results can thus be obtained with high efficiency.

In step S706, the image processing unit 305 may predict the time period until the predetermined pupil diameter is detected, based on a plurality of measurement results of the pupil diameter at different times. For example, the image processing unit 305 calculates an approximate curve from the plurality of measurement results of the pupil diameter at different times, and calculates the time until the predetermined pupil diameter is detected. The image processing unit 305 then may count the remaining time period until the predetermined pupil diameter is detected, and output the remaining time using the display unit 310 and/or the audio output unit 350.

The order of the inspections in the inspection protocol may be changed based on the measurement result of the pupil diameter measured in step S706. For example, if an inspection that can be performed with a pupil diameter smaller than the measurement result of the pupil diameter is scheduled after the inspection put on standby in the inspection protocol, the inspection that can be performed with the smaller pupil diameter may be performed first.

As described above, the present exemplary embodiment can provide an ophthalmic apparatus capable of obtaining stable inspection results with high efficiency by successive inspections.

(Modifications: Result Output)

When the imaging condition is poor, reinspection is performed. However, the images obtained by the reinspection may not be desirable results. In the foregoing various exemplary embodiments, the images obtained by the reinspection and the images obtained before the reinspection may be displayed next to each other for the user's selection.

Figure 16:
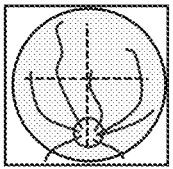
FIGS. 16A and 16B are diagrams each illustrating an example of an output screen according to a modification.
Figure 17:
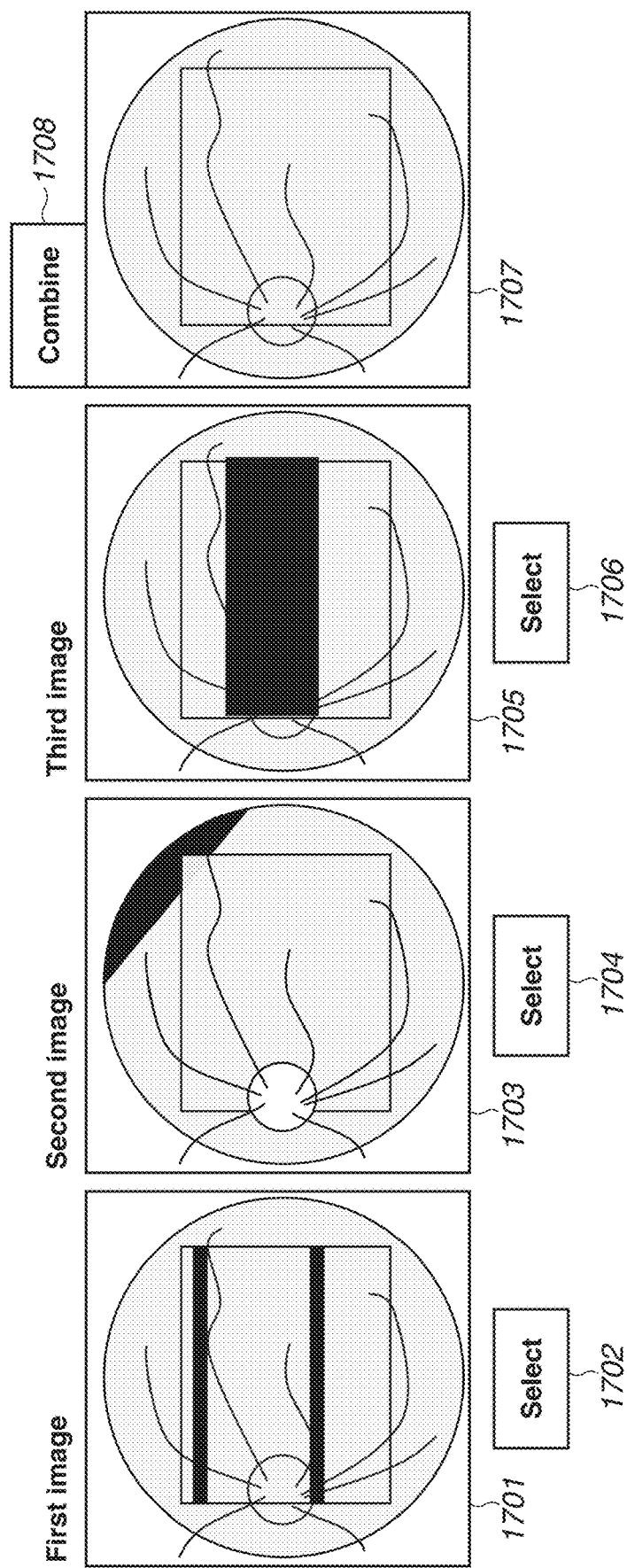
FIG. 17 is a diagram illustrating an example of the output screen according to the modification.

FIGS. 16A and 16B illustrate two display examples of an inspection result list. In the examples, five inspections are performed, with inspection 3 retried once and inspection 4 retried twice. In FIG. 16A, the number of icons additionally displayed indicates the number of reinspections. In FIG. 16B, the hatching indicates that a reinspection or reinspections is/are performed. In a case where the field of inspection 4 is clicked, captured images 1701, 1703, and 1705 are displayed as illustrated in FIG. 17. One of the images 1701, 1703, and 1705 can be selected by clicking on a corresponding one of selection buttons 1702, 1704, or 1706. A button 1708 for issuing an editing instruction may be displayed, and a new image may be generated by clicking on the button 1708 to perform editing. In the illustrated example, the images 1701 and 1703 are selected by the selection buttons 1702 and 1704, and a combined image 1707 is generated. The selected images may be indicated by color frames. The selected buttons may be displayed in different color. If the inspection is ordered via a network, the reinspection images and the images before the reinspections may be transmitted as inspection results to the personal computer issued the order, and the doctor may perform a selection on the screen of the personal computer.

The following additional notes are disclosed as other aspects and selective features of the present invention related to the foregoing various exemplary embodiments and modifications:

(Additional Note 1-1)

An ophthalmic apparatus includes an inspection unit configured to inspect an eye to be inspected, a driving unit configured to drive the inspection unit, a selection unit configured to select an inspection protocol from among a plurality of different inspection protocols, based on an instruction from a user, the plurality of different instruction protocols each defining a series of control procedures for performing a plurality of inspections including an alignment adjustment for aligning the inspection unit with the eye to be inspected, and a control unit configured to start control of the inspection unit and the driving unit based on the selected inspection protocol in response to a predetermined condition, wherein the control unit is configured to display a result of the plurality of inspections and display information for accepting an instruction to perform at least one of the plurality of inspections based on the selected inspection protocol on a display unit.

(Additional Note 1-2)

An ophthalmic apparatus includes an inspection unit configured to inspect an eye to be inspected, a driving unit configured to drive the inspection unit, and a control unit configured to start control of the inspection unit and the driving unit based on an inspection protocol in response to a predetermined condition, the inspection protocol defining a series of control procedures for performing a plurality of inspections including an alignment adjustment for aligning the inspection unit with the eye to be inspected. The control unit is configured to display results of the plurality of inspections and display information for accepting an instruction to retry a part of the plurality of inspections on a display unit.

(Additional Note 1-3)

The ophthalmic apparatus may further include a selection unit configured to select an inspection protocol from among a plurality of different inspection protocols, based on an instruction from a user, the plurality of different inspection protocols each defining a series of control procedures for performing a plurality of inspections including the alignment adjustment for aligning the inspection unit with the eye to be inspected. The control unit may be configured to start the control of the inspection unit and the driving unit based on the selected inspection protocol in response to the predetermined condition.

(Additional Note 1-4)

The display unit may be a touch panel, and the display information may be a button for a user to tap on.

(Additional Note 1-5)

The control unit may display a result of one inspection among the results of the plurality of inspections and the display information for accepting an instruction to perform the one inspection on the display unit in association with each other.

(Additional Note 1-6)

The control unit may be configured to display, on the display unit, a first screen displayed when an adjustment operation including the alignment adjustment is in progress and a second screen displaying the result of the plurality of inspections. The second screen may include a plurality of screens to be switched by an instruction from the user.

(Additional Note 1-7)

The control may display a first screen and a second screen on the display unit, the first screen being displayed when an adjustment operation including the alignment adjustment is in progress, the second screen displaying the results of the plurality of inspections. The second screen may include a plurality of screens to be switched by an instruction from a user or to be switched after a lapse of a predetermined time.

(Additional Note 1-8)

The control unit may display a result of one inspection among the results of the plurality of inspections and the display information for accepting an instruction to perform the one inspection on one of the plurality of screens included in the second screen.

(Additional Note 1-9)

The one screen may be generated each time one of the plurality of inspections ends.

(Additional Note 1-10)

One of the plurality of inspections included in the inspection protocol other than a last may be selected by the user. The control unit may display the second screen displaying the results of the plurality of inspections when the inspection selected by the user ends.

(Additional Note 1-11)

The control unit may suspend the control of the inspection unit and the driving unit based on the inspection protocol in response to an instruction from a user, and in a case where the control of the inspection unit and the driving unit based on the inspection protocol is suspended, resume the control of the inspection unit and the driving unit based on the inspection protocol in response to an instruction from the user.

(Additional Note 1-12)

An ophthalmic apparatus include an inspection unit configured to inspect an eye to be inspected, a driving unit configured to drive the inspection unit, and a control unit configured to start control of the inspection unit and the driving unit based on an inspection protocol in response to a predetermined condition, the inspection protocol defining a series of control procedures for performing a plurality of inspections including an alignment adjustment for aligning the inspection unit with the eye to be inspected. The control unit is configured to suspend the control of the inspection unit and the driving unit based on the inspection protocol in response to an instruction from a user, and in a case where the control of the inspection unit and the driving unit based on the inspection protocol is suspended, resume the control of the inspection unit and the driving unit based on the inspection protocol in response to an instruction from the user.

(Additional Note 1-13)

The control unit may resume, in a case where an instruction to resume the control of the inspection unit and the driving unit based on the inspection protocol is received, the control of the inspection unit and the driving unit from the suspended inspection among the plurality of inspections defined by the inspection protocol.

(Additional Note 1-14)

The control unit may put, in a case where an instruction to suspend the control of the inspection unit and the driving unit based on the inspection protocol is received, the inspection unit on standby at a position where the inspection unit is when the instruction is received.

(Additional Note 1-15)

The ophthalmic apparatus further includes a detection unit configured to detect relative position information about the eye to be inspected and the inspection unit. The detection unit may continue detecting the relative position information even in a case where the control of the inspection unit and the driving unit based on the inspection protocol is suspended.

(Additional Note 1-16)

The ophthalmic apparatus may further include a notification unit configured to issue a warning in a case where the detection unit fails to detect the relative position information.

(Additional Note 1-17)

The control unit may control the driving unit to maintain the eye to be inspected within a range where the detection unit detects the relative position information.

(Additional Note 1-18)

The predetermined condition may be an instruction from a user.

(Additional Note 1-19)

The control unit may change the inspections included in the inspection protocol based on an instruction from a user.

(Additional Note 1-20)

The control unit may put, after at least one of the plurality of inspections ends, the inspection unit on standby at a predetermined position.

(Additional Note 1-21)

The position where the inspection unit is on standby may be either a position where the inspection unit is when the at least one inspection ends or a position to which the inspection unit is moved from the position where the inspection unit is when the at least one inspection ends in a direction in which the inspection unit moves away from the eye to be inspected along a direction of an optical axis of an optical system of the inspection unit.

(Additional Note 1-22)

In a case where the inspection protocol includes inspections on both left and right eyes and the at least one inspection is a last inspection on the right eye, the position where the inspection unit is on standby may be either a position where the inspection unit is when the at least one inspection ends or a position where the inspection unit is closer to the left eye than at the position where the inspection unit is when the at least one inspection ends, and in a case where the inspection protocol includes inspections on both the left and right eyes and the at least one inspection is a last inspection on the left eye, the position where the inspection unit is on standby may be either the position where the inspection unit is when the at least one inspection ends or a position where the inspection unit is closer to the right eye than at the position where the inspection unit is when the at least one inspection ends.

(Additional Note 1-23)

The control unit may align the inspection unit with both right and left eyes of an examinee. The inspection protocol may define execution of inspections on both the right and left eyes.

(Additional Note 1-24)

The inspection unit may perform an optical coherence tomography (OCT) inspection to obtain information about a characteristic of the eye to be inspected by using combined light obtained by combining return light from the eye to be inspected irradiated with measurement light with reference light. The inspection protocol may define an imaging condition under which the OCT inspection included in the plurality of inspections is performed. The control unit may cause the inspection unit and the driving unit to perform an adjustment operation including an alignment adjustment, a focus adjustment, and a coherence gate adjustment.

(Additional Note 1-25)

The imaging condition may be at least one of a scan pattern, a portion to be scanned, and a scan range.

(Additional Note 1-26)

The inspection protocol may be an inspection protocol defining execution of a plurality of different inspections including fundus imaging using visible light.

(Additional Note 1-27)

The inspection protocol may be an inspection protocol defining execution of both an OCT inspection for obtaining information about a characteristic of the eye to be inspected by using combined light obtained by combining return light from the eye to be inspected irradiated with measurement light with reference light and fundus imaging using visible light.

(Additional Note 1-28)

An ophthalmic apparatus includes an inspection unit configured to perform OCT imaging for obtaining a tomographic image of an eye to be inspected and fundus imaging using visible light, the OCT imaging using combined light obtained by combining return light from the eye to be inspected irradiated with measurement light with reference light, a driving unit configured to drive the inspection unit, a selection unit configured to select an imaging condition from among a plurality of imaging conditions related to the OCT imaging, based on an instruction from a user, and a control unit configured to issue an instruction to automatically perform an adjustment operation, the OCT imaging based on the selected imaging condition, and the fundus imaging in order in response to a predetermined condition, the adjustment operation including an alignment adjustment, a focus adjustment, and a coherence gate adjustment, the control unit being configured to display an OCT image of the eye to be inspected captured by the OCT imaging based on the selected imaging condition, a fundus image of the eye to be inspected captured by the fundus imaging, and display information for accepting an instruction to perform at least either of the OCT imaging based on the selected imaging condition and the fundus imaging on a display unit.

(Additional Note 1-29)

A method for controlling an ophthalmic apparatus including an inspection unit for inspecting an eye to be inspected and a driving unit for driving the inspection unit, the method includes selecting an inspection protocol from among a plurality of different inspection protocols based on an instruction from a user, the plurality of different inspection protocols each defining a series of control procedures for performing a plurality of inspections including an alignment adjustment for aligning the inspection unit with the eye to be inspected, starting control of the inspection unit and the driving unit based on the selected inspection protocol in response to a predetermined condition, and displaying a result of the plurality of inspections and display information for accepting an instruction to perform at least one of the plurality of inspections based on the selected inspection protocol on a display unit.

(Additional Note 1-30)

A method for controlling an ophthalmic apparatus including an inspection unit for inspecting an eye to be inspected and a driving unit for driving the inspection unit, the method includes starting control of the inspection unit and the driving unit based on an inspection protocol in response to a predetermined condition, the inspection protocol defining a series of control procedures for performing a plurality of inspections including an alignment adjustment for aligning the inspection unit with the eye to be inspected and displaying results of the plurality of inspections and display information for accepting an instruction to retry a part of the plurality of inspections on a display unit.

(Additional Note 1-31)

A method for controlling an ophthalmic apparatus including an inspection unit for inspecting an eye to be inspected and a driving unit for driving the inspection unit, the method includes starting control of the inspection unit and the driving unit based on an inspection protocol in response to a predetermined condition, the inspection protocol defining a series of control procedures for performing a plurality of inspections including an alignment adjustment for aligning the inspection unit with the eye to be inspected, suspending the control of the inspection unit and the driving unit based on the inspection protocol in response to an instruction from a user, and in a case where the control of the inspection unit and the driving unit based on the inspection protocol is suspended, resume the control of the inspection unit and the driving unit based on the inspection protocol in response to an instruction from the user.

(Additional Note 1-32)

A method for controlling an ophthalmic apparatus including an inspection unit for performing OCT imaging for obtaining a tomographic image of an eye to be inspected and fundus imaging using visible light, the OCT imaging using combined light obtained by combining return light from the eye to be inspected irradiated with measurement light with reference light, and a driving unit for driving the inspection unit, the method includes selecting an imaging condition from among a plurality of imaging conditions related to the OCT imaging based on an instruction from a user, issuing an instruction to automatically perform an adjustment operation, the OCT imaging based on the selected imaging condition, and the fundus imaging in order in response to a predetermined condition, the adjustment operation including an alignment adjustment, a focus adjustment, and coherence gate adjustment, and displaying an OCT image of the eye to be inspected captured by the OCT imaging based on the selected imaging condition, a fundus image of the eye to be inspected captured by the fundus imaging, and display information for accepting an instruction to perform at least either of the OCT imaging based on the selected imaging condition and the fundus imaging on a display unit.

(Additional Note 1-33)

A program may cause a computer to perform the method for controlling an ophthalmic apparatus.

(Additional Note 2-1)

An ophthalmic apparatus includes an inspection unit configured to inspect an eye to be inspected, an alignment unit configured to align the inspection unit with the eye to be inspected, a position information detection unit configured to detect relative position information about the eye to be inspected and the inspection unit, a storage unit configured to store an inspection sequence defining a series of control procedures for performing a plurality of inspections including an alignment operation for aligning the inspection unit with the eye to be inspected, and a control unit configured to control alignment by the alignment unit based on the relative position information and control the inspection unit to perform the plurality of inspections based on the stored inspection sequence, wherein the control unit is configured to put, after a first inspection using visible light among the plurality of inspections to be performed is performed, the inspection unit on standby for a predetermined time before a second inspection subsequent to the first inspection is performed.

(Additional Note 2-2)

An ophthalmic apparatus includes an inspection unit configured to optically inspect an eye to be inspected, an observation unit including at least two imaging units each configured to capture an image of an anterior eye part of the eye to be inspected in a direction different from an optical axis of the inspection unit, an alignment unit configured to align the inspection unit with the eye to be inspected, a transformation unit configured to transform the image captured by each of the at least two imaging units into an image captured in a direction of the optical axis of the inspection unit, and a control unit configured to display an alignment reference mark superimposed on the transformed image, the alignment reference mark serving as a reference in aligning the inspection unit with the eye to be inspected.

(Additional Note 2-3)

The alignment reference mark may be a mark indicating a size of a pupil diameter required for the inspections.

(Additional Note 2-4)

The ophthalmic apparatus may further include a driving unit configured to drive the alignment unit, a position information detection unit configured to detect relative position information about the eye to be inspected and the inspection unit based on an output of the observation unit, a storage unit configured to store an inspection sequence defining a series of control procedures for performing a plurality of inspections including an alignment operation for aligning the inspection unit with the eye to be inspected, a start acceptance unit configured to accept an instruction to start the stored inspection sequence, and a control unit configured to control the inspection unit to perform the plurality of inspections, wherein in response to the instruction, the control unit is configured to control the driving unit based on the relative position information and control the inspection unit to perform the inspections based on the stored inspection sequence, and after a first inspection using visible light among the plurality of inspections to be performed is performed, put the inspection unit on standby for a predetermined time before a second inspection subsequent to the first inspection is performed.

(Additional Note 2-5)

An ophthalmic apparatus includes an observation unit configured to observe an anterior eye part of an eye to be inspected of an examinee, an inspection unit configured to inspect the eye to be inspected, an alignment unit configured to align the inspection unit with the eye to be inspected, a driving unit configured to drive the alignment unit, a position information detection unit configured to detect relative position information about the eye to be inspected and the inspection unit based on an output of the observation unit, a storage unit configured to store an inspection sequence defining a series of control procedures for performing a plurality of inspections including an alignment operation to align the inspection unit with the eye to be inspected, a start acceptance unit configured to accept an instruction to start the stored inspection sequence, and a control unit configured to control, in response to the instruction, the driving unit based on the relative position information and the inspection unit to perform the inspections based on the stored inspection sequence, wherein the control unit is configured to put, after a first inspection using visible light among the plurality of inspections to be performed is performed, the inspection unit on standby for a predetermined time before a second inspection subsequent the first inspection is performed.
(Additional Note 2-6)

The predetermined time may be a standby time varying depending on at least one of types and inspection parameters of the first inspection and the second inspection.
(Additional Note 2-7)

The inspection parameters may be information about an amount of the visible light to be used in the first inspection and a minimum pupil diameter for the second inspection.
(Additional Note 2-8)

The control unit may be configured to put the inspection unit on standby in front of the eye to be inspected on which the second inspection is performed.
(Additional Note 2-9)

The ophthalmic apparatus may include a pupil diameter measurement unit configured to measure a pupil diameter of the eye to be inspected based on the image captured by one of the at least two imaging units. The control unit may be configured to perform the second inspection, in a case where the pupil diameter of the eye to be inspected measured by the pupil diameter measurement unit is a predetermined pupil diameter.
(Additional Note 2-10)

The ophthalmic apparatus may further include a prediction unit configured to predict time until the pupil diameter of the eye to be inspected reaches the predetermined pupil diameter, based on an output of the pupil diameter measurement unit, a counting unit configured to count remaining time until the pupil diameter of the eye to be inspected reaches the predetermined pupil diameter, and a notification unit configured to make a notification of the remaining time counted by the counting unit.
(Additional Note 2-11)

The control unit may be configured to perform, in a case where the pupil diameter of the eye to be inspected measured by the pupil diameter measurement unit during the standby is smaller than the predetermined pupil diameter and an inspection to be performed with a smaller pupil diameter is scheduled after the inspection currently on the standby in the inspection sequence, the inspection to be performed with the smaller pupil diameter first.
(Additional Note 2-12)

An ophthalmic apparatus includes an inspection unit configured to inspect an eye to be inspected, an alignment unit configured to align the inspection unit with the eye to be inspected, a position information detection unit configured to detect relative position information about the eye to be inspected and the inspection unit, a storage unit configured to store an inspection sequence defining a series of control procedures for performing a plurality of inspections including an alignment operation to align the inspection unit with the eye to be inspected, a control unit configured to control alignment by the alignment unit based on the relative position information and control the inspection unit to perform the inspections based on the stored inspection sequence, and an acceptance unit configured to accept an instruction to suspend an operation and put the operation on standby for a predetermined time while the inspection sequence is in operation.
(Additional Note 2-13)

The ophthalmic apparatus may further include a setting unit configured to set the predetermined time.
(Additional Note 2-14)

The control unit may be configured to put the inspection unit on standby in front of the eye to be inspected scheduled to be aligned next or currently in process of alignment.
(Additional Note 2-15)

The ophthalmic apparatus may further include an extension switch configured to give an instruction to extend the standby time by a predetermined time. The standby time may be extended by a predetermined time each time the extension switch is pressed.
(Additional Note 2-16)

The ophthalmic apparatus may further include a cancellation switch configured to issue an instruction to cancel the standby.
(Additional Note 2-17)

The inspection unit is a composite inspection unit configured to perform a plurality of different inspections. The inspection using the visible light may be an inspection to illuminate a fundus of the eye to be inspected and obtain a fundus image of the eye to be inspected.
(Additional Note 2-18)

The ophthalmic apparatus may further include a counting unit configured count remaining time of the standby time, and a notification unit configured to issue a notification of the remaining time counted by the counting unit.
(Additional Note 2-19)

The notification unit may be the display unit configured to display the remaining time.
(Additional Note 2-20)

The notification unit may be a unit configured to issue a notification of the remaining time by voice.
(Additional Note 2-21)

The position information detection unit may be configured to continue detecting the relative position information during the standby. The control unit may be configured to control, in a case where a position of the eye to be inspected approaches a limit of a detection range of the position information detection unit, the alignment unit to maintain the position of the eye to be inspected within the detection range of the position information detection unit.
(Additional Note 2-22)

A method for controlling an ophthalmic apparatus including an inspection unit for inspecting an eye to be inspected and an alignment unit for aligning the inspection unit with the eye to be inspected, the method includes detecting relative position information about the eye to be inspected and the inspection unit, storing an inspection sequence defining a series of control procedures for performing a plurality of inspections including an alignment operation for aligning the inspection unit with the eye to be inspected, and controlling alignment by the alignment unit based on the relative position information and controlling the inspection unit to perform the inspections based on the stored inspection sequence, wherein after a first inspection using visible light among the plurality of inspections to be performed is performed, the inspection unit is put on standby for a predetermined time before a second inspection subsequent to the first inspection is performed.

(Additional Note 2-23)

A method for controlling an ophthalmic apparatus including at least two imaging units each configured to capture an image of an anterior eye part of an eye to be inspected in a direction different from an optical axis of an inspection unit configured to optically inspect the eye to be inspected, the method includes aligning the inspection unit with the eye to be inspected, transforming the image captured by each of the at least two imaging units into an image captured in a direction of the optical axis of the inspection unit, and displaying an alignment reference mark on the transformed image in a superimposed manner, the alignment reference mark serving as a reference in the aligning.

(Additional Note 2-24)

A method for controlling an ophthalmic apparatus including an observation unit configured to observe an anterior eye part of an eye to be inspected of an examinee, an inspection unit configured to inspect the eye to be inspected, an alignment unit configured to align the inspection unit with the eye to be inspected, a driving unit configured to drive the alignment unit, a position information detection unit configured to detect relative position information about the eye to be inspected and the inspection unit based on an output of the observation unit, a storage unit configured to store an inspection sequence defining a series of control procedures for performing a plurality of inspections including an alignment operation for aligning the inspection unit with the eye to be inspected, a start acceptance unit configured to accept an instruction to start the stored inspection sequence, and a control unit configured to control, in response to the instruction, the driving unit based on the relative position information and the inspection unit to perform the inspections based on the stored inspection sequence, the method includes, after a first inspection using visible light among the plurality of inspections to be performed is performed, putting the inspection unit on standby for a predetermined time before a second inspection subsequent to the first inspection is performed.

(Additional Note 3-1)

An ophthalmic apparatus configured to automatically perform a plurality of inspections using an inspection unit on an eye to be inspected includes an inspection device configured to perform the plurality of inspections in order by using the inspection unit, an acceptance unit configured to accept a specific instruction between a first inspection and a second inspection, and a control unit configured to control the inspection device based on the instruction.

(Additional Note 3-2)

The ophthalmic apparatus may further include an alignment unit configured to align the inspection unit with the eye to be inspected, a position information detection unit configured to detect relative position information about the eye to be inspected and the inspection unit, and a storage unit configured to store an inspection sequence defining a series of control procedures for performing a plurality of inspections including an alignment operation for aligning the inspection unit with the eye to be inspected. The control unit may be configured to control alignment by the alignment unit based on the relative position information and control the inspection unit to perform the inspections based on the stored inspection sequence, and after the first inspection using visible light among the plurality of inspections to be performed is performed, put the inspection unit on standby before the second inspection subsequent to the first inspection is performed.

(Additional Note 3-3)

The ophthalmic apparatus may further include an observation unit including at least two imaging units each configured to capture an image of an anterior eye part of the eye to be inspected in a direction different from an optical axis of the inspection unit, an alignment unit configured to align the inspection unit with the eye to be inspected, a transformation unit configured to transform the image captured by each of the at least two imaging units into an image captured in a direction of the optical axis of the inspection unit, and an output control unit configured to display an alignment reference mark on the transformed image in a superimposed manner, the alignment reference mark serving as a reference in aligning the inspection unit with the eye to be inspected.

(Additional Note 3-4)

A method for controlling an ophthalmic apparatus configured to automatically perform a plurality of inspections using an inspection unit on an eye to be inspected, the method includes performing the plurality of inspections in order by using the inspection unit, accepting a specific instruction between a first inspection and a second inspection, and controlling the inspection device based on the instruction.

(Additional Note 3-5)

The ophthalmic apparatus further includes a driving unit configured to drive the inspection unit, and a selection unit configured to select an inspection sequence from among a plurality of different inspection sequences based on an instruction from a user, the plurality of different inspection sequences each defining a series of control procedures for performing a plurality of inspections including an alignment adjustment for aligning the inspection unit with the eye to be inspected. The control unit may be configured to start control of the inspection unit and the driving unit based on the selected inspection sequence in response to a predetermined condition, and display a result of the plurality of inspections and display information for accepting an instruction to perform at least one of the plurality of inspections based on the selected inspection sequence on a display unit.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2020-176077, filed Oct. 20, 2020, No. 2020-204332, filed Dec. 9, 2020, and No. 2021-135543, filed Aug. 23, 2021, which are hereby incorporated by reference herein in their entirety.

What is claimed is:

1. An ophthalmic apparatus comprising:
an inspection unit configured to inspect an eye to be inspected;
a driving unit configured to drive the inspection unit;
a selection unit configured to select an inspection protocol from among a plurality of different inspection protocols based on an instruction from a user, the plurality of different inspection protocols each defining a series of control procedures for performing a plurality of inspections including an alignment adjustment for aligning the inspection unit with the eye to be inspected; and
a control unit configured to start control of the inspection unit and the driving unit based on the selected inspection protocol in response to a predetermined condition, wherein the control unit is configured to display results of the plurality of inspections and display information for accepting an instruction to retry a part of the plurality of inspections on a display unit.

2. The ophthalmic apparatus according to claim 1, wherein the display unit is a touch panel, and
wherein the display information includes a button tapped by a user.

3. The ophthalmic apparatus according to claim 1, wherein the control unit is configured to display a result of one inspection among the results of the plurality of inspections and the display information for accepting an instruction to perform the one inspection on the display unit in association with each other.

4. The ophthalmic apparatus according to claim 1, wherein the control unit is configured to display a first screen and a second screen on the display unit, the first screen being displayed when an adjustment operation including the alignment adjustment is in progress, the second screen displaying the results of the plurality of inspections, and
wherein the second screen includes a plurality of screens to be switched by an instruction from a user or to be switched after a lapse of a predetermined time.

5. The ophthalmic apparatus according to claim 4, wherein the control unit is configured to display a result of one inspection among the results of the plurality of inspections and the display information for accepting an instruction to perform the one inspection on one of the plurality of screens included in the second screen.

6. The ophthalmic apparatus according to claim 5, wherein the one screen is generated each time one of the plurality of inspections ends.

7. The ophthalmic apparatus according to claim 4, wherein one of the plurality of inspections included in the inspection protocol other than a last is selected by the user, and
wherein the control unit is configured to display the second screen displaying the results of the plurality of inspections when the inspection selected by the user ends.

8. The ophthalmic apparatus according to claim 1, wherein the control unit is configured to suspend the control of the inspection unit and the driving unit based on the inspection protocol in response to an instruction from a user, and in a case where the control of the inspection unit and the driving unit based on the inspection protocol is suspended, resume the control of the inspection unit and the driving unit based on the inspection protocol in response to an instruction from the user.

9. The ophthalmic apparatus according to claim 8, wherein the control unit is configured to resume, in a case where an instruction to resume the control of the inspection unit and the driving unit based on the inspection protocol is received, the control of the inspection unit and the driving unit from the suspended inspection among the plurality of inspections defined by the inspection protocol.

10. The ophthalmic apparatus according to claim 8, wherein the control unit is configured to put, in a case where an instruction to suspend the control of the inspection unit and the driving unit based on the inspection protocol is received, the inspection unit on standby at a position where the inspection unit is when the instruction is received.

11. The ophthalmic apparatus according to claim 8, further comprising:
a detection unit configured to detect relative position information about the eye to be inspected and the inspection unit,
wherein the detection unit is configured to continue detecting the relative position information even in a case where the control of the inspection unit and the driving unit based on the inspection protocol is suspended.

12. The ophthalmic apparatus according to claim 11, further comprising:
a notification unit configured to issue a warning in a case where the detection unit fails to detect the relative position information.

13. The ophthalmic apparatus according to claim 11, wherein the control unit is configured to control the driving unit to maintain the eye to be inspected within a range where the detection unit detects the relative position information.

14. The ophthalmic apparatus according to claim 1, wherein the predetermined condition includes an instruction from a user.

15. The ophthalmic apparatus according to claim 1, wherein the control unit is configured to change the inspections included in the inspection protocol based on an instruction from a user.

16. The ophthalmic apparatus according to claim 1, wherein the control unit is configured to put, after at least one of the plurality of inspections ends, the inspection unit on standby at a predetermined position.

17. The ophthalmic apparatus according to claim 16, wherein the position where the inspection unit is on standby is either a position where the inspection unit is when the at least one inspection ends or a position to which the inspection unit is moved from the position where the inspection unit is when the at least one inspection ends in a direction in which the inspection unit moves away from the eye to be inspected along a direction of an optical axis of an optical system of the inspection unit.

18. The ophthalmic apparatus according to claim 16, wherein in a case where the inspection protocol includes inspections on both left and right eyes and the at least one inspection is a last inspection on the right eye, the position where the inspection unit is on standby is either where the inspection unit is when the at least one inspection ends or where the inspection unit is closer to the left eye than where the inspection unit is when the at least one inspection ends, and in a case where the inspection protocol includes inspections on both the left and right eyes and the at least one inspection is a last inspection on the left eye, the position where the inspection unit is on standby is either where the inspection unit is when the at least one inspection ends or where the inspection unit is closer to the right eye than at the position where the inspection unit is when the at least one inspection ends.

19. The ophthalmic apparatus according to claim 1,
   wherein the control unit is configured to align the inspection unit with both right and left eyes of an examinee, and
   wherein the inspection protocol defines execution of inspections on both the right and left eyes.

20. The ophthalmic apparatus according to claim 1,
   wherein the inspection unit is configured to perform an optical coherence tomography (OCT) inspection to obtain information about a characteristic of the eye to be inspected by using combined light obtained by combining return light from the eye to be inspected irradiated with measurement light with reference light,
   wherein the inspection protocol defines an imaging condition under which the OCT inspection included in the plurality of inspections is performed, and
   wherein the control unit is configured to cause the inspection unit and the driving unit to perform an adjustment operation including the alignment adjustment, a focus adjustment, and a coherence gate adjustment.

21. The ophthalmic apparatus according to claim 20, wherein the imaging condition is at least one of a scan pattern, a portion to be scanned, and a scan range.

22. The ophthalmic apparatus according to claim 1, wherein the inspection protocol define execution of both an OCT inspection for obtaining information about a characteristic of the eye to be inspected by using combined light obtained by combining return light from the eye to be inspected irradiated with measurement light with reference light and fundus imaging using visible light.

23. A method for controlling an ophthalmic apparatus including an inspection unit for inspecting an eye to be inspected and a driving unit for driving the inspection unit and a selection unit configured to select an inspection protocol from among a plurality of different inspection protocols each defining a series of control procedures for performing a plurality of inspections including an alignment adjustment for aligning the inspection unit with the eye to be inspected, the method comprising:
   starting control of the inspection unit and the driving unit based on the selected inspection protocol in response to a predetermined condition; and
   displaying results of the plurality of inspections and display information for accepting an instruction to retry a part of the plurality of inspections on a display unit.

24. A non-transitory computer-readable storage medium storing a program for causing a computer to execute the method according to claim 23.

* * * * *